US011564735B2

(12) United States Patent
Placek et al.

(10) Patent No.: US 11,564,735 B2
(45) Date of Patent: *Jan. 31, 2023

(54) NEEDLE AND FINE DEPLOYMENT MECHANISM

(71) Applicant: Gynesonics, Inc., Redwood City, CA (US)

(72) Inventors: Brian Placek, Manhattan, KS (US); Robert K. Deckman, San Bruno, CA (US)

(73) Assignee: Gynesonics, Inc., Redwood City, CA (US)

( * ) Notice: Subject to any disclaimer, the term of this patent is extended or adjusted under 35 U.S.C. 154(b) by 150 days.

This patent is subject to a terminal disclaimer.

(21) Appl. No.: 16/417,193

(22) Filed: May 20, 2019

(65) Prior Publication Data

US 2019/0269456 A1 Sep. 5, 2019

Related U.S. Application Data

(60) Continuation of application No. 13/589,956, filed on Aug. 20, 2012, now Pat. No. 10,321,951, which is a
(Continued)

(51) Int. Cl.
*A61B 18/14* (2006.01)
*A61B 18/00* (2006.01)
(Continued)

(52) U.S. Cl.
CPC .......... *A61B 18/1477* (2013.01); *A61B 2018/00547* (2013.01); *A61B 2018/00559* (2013.01);
(Continued)

(58) Field of Classification Search
CPC ........ A61B 18/1477; A61B 2090/3784; A61B 2034/2063; A61B 2018/00547;
(Continued)

(56) References Cited

U.S. PATENT DOCUMENTS

| 4,802,487 A | 2/1989 | Martin et al. |
| 4,936,281 A | 6/1990 | Stasz |

(Continued)

FOREIGN PATENT DOCUMENTS

| WO | WO-9717105 A1 | 5/1997 |
| WO | WO-9811834 A1 | 3/1998 |

(Continued)

OTHER PUBLICATIONS

Lumsden et al. 1998 in "Bailliere's Clinical Obstetrics and Genecology" vol. 12 chap.2 p. 177-195 (Year: 1998).*
(Continued)

*Primary Examiner* — Colin T. Sakamoto
*Assistant Examiner* — Patrick M Mehl
(74) *Attorney, Agent, or Firm* — Wilson Sonsini Goodrich & Rosati

(57) ABSTRACT

A needle electrode deployment shaft includes a central member and a plurality of needle electrodes. The central member has a plurality of needle advancement channels formed therein. The needle electrodes are disposed within the advancement channels and each advancement channel terminates in a ramp portion which deflects the needles radially outwardly as they are axially advanced. The ramps may be spirally or acutely configured in order to increase the distance through which the needles may be bent as they are axially advanced. Additionally, the central member may have a radially reduced distal tip in order to decrease tissue insertion forces.

19 Claims, 15 Drawing Sheets

FIG. 1

Related U.S. Application Data division of application No. 12/712,969, filed on Feb. 25, 2010, now Pat. No. 8,262,574.

(60) Provisional application No. 61/156,270, filed on Feb. 27, 2009.

(51) Int. Cl.
*A61B 34/20* (2016.01)
*A61B 90/00* (2016.01)

(52) U.S. Cl.
CPC ............ *A61B 2018/00577* (2013.01); *A61B 2018/143* (2013.01); *A61B 2018/1427* (2013.01); *A61B 2018/1475* (2013.01); *A61B 2034/2063* (2016.02); *A61B 2090/3784* (2016.02)

(58) Field of Classification Search
CPC .......... A61B 2018/00559; A61B 2018/00577; A61B 2018/1427; A61B 2018/143; A61B 2018/1475; A61B 18/18; A61B 2018/1425; A61B 2018/1437; A61B 2018/1432; A61B 2018/1435; A61B 2018/147

See application file for complete search history.

(56) References Cited

U.S. PATENT DOCUMENTS

| | | |
|---|---|---|
| 5,372,587 A | 12/1994 | Hammerslag et al. |
| 5,456,689 A | 10/1995 | Kresch et al. |
| 5,469,853 A | 11/1995 | Law et al. |
| 5,471,988 A | 12/1995 | Fujio et al. |
| 5,492,126 A | 2/1996 | Hennige et al. |
| 5,527,331 A | 6/1996 | Kresch et al. |
| 5,607,389 A | 3/1997 | Edwards et al. |
| 5,662,664 A | 9/1997 | Gordon et al. |
| 5,666,954 A | 9/1997 | Chapelon et al. |
| 5,697,897 A | 12/1997 | Buchholtz et al. |
| 5,730,752 A | 3/1998 | Alden et al. |
| 5,741,287 A | 4/1998 | Alden et al. |
| 5,752,518 A | 5/1998 | McGee et al. |
| 5,769,880 A | 6/1998 | Truckai et al. |
| 5,860,974 A | 1/1999 | Abele et al. |
| 5,863,294 A | 1/1999 | Alden |
| 5,873,828 A | 2/1999 | Fujio et al. |
| 5,876,340 A | 3/1999 | Tu et al. |
| 5,876,399 A | 3/1999 | Chia et al. |
| 5,891,137 A | 4/1999 | Chia et al. |
| 5,906,615 A | 5/1999 | Thompson |
| 5,908,385 A | 6/1999 | Chechelski et al. |
| 5,916,198 A | 6/1999 | Dillow |
| 5,957,941 A | 9/1999 | Ream |
| 5,964,740 A | 10/1999 | Ouchi |
| 5,979,452 A | 11/1999 | Fogarty et al. |
| 5,979,453 A | 11/1999 | Savage et al. |
| 5,984,942 A | 11/1999 | Alden et al. |
| 6,002,968 A | 12/1999 | Edwards |
| 6,007,499 A | 12/1999 | Martin et al. |
| 6,032,673 A | 3/2000 | Savage et al. |
| 6,039,748 A | 3/2000 | Savage et al. |
| 6,050,992 A | 4/2000 | Nichols |
| 6,059,766 A | 5/2000 | Greff |
| 6,077,257 A | 6/2000 | Edwards et al. |
| 6,083,169 A | 7/2000 | Hansen |
| 6,126,665 A | 10/2000 | Yoon |
| 6,141,577 A | 10/2000 | Rolland et al. |
| 6,146,378 A | 11/2000 | Mikus et al. |
| 6,158,250 A | 12/2000 | Tibbals, Jr. et al. |
| 6,171,249 B1 | 1/2001 | Chin et al. |
| 6,190,383 B1 | 2/2001 | Schmaltz et al. |
| 6,193,714 B1 | 2/2001 | McGaffigan et al. |
| 6,211,153 B1 | 4/2001 | Garnick et al. |
| 6,238,336 B1 | 5/2001 | Ouchi |
| 6,254,601 B1 | 7/2001 | Burbank et al. |
| 6,280,441 B1 | 8/2001 | Ryan |
| 6,296,639 B1 | 10/2001 | Truckai et al. |
| 6,306,097 B1 | 10/2001 | Park et al. |
| 6,306,129 B1 | 10/2001 | Little et al. |
| 6,315,741 B1 | 11/2001 | Martin et al. |
| 6,379,348 B1 | 4/2002 | Onik |
| 6,405,732 B1 | 6/2002 | Edwards et al. |
| 6,419,648 B1 | 7/2002 | Vitek et al. |
| 6,419,653 B2 | 7/2002 | Edwards et al. |
| 6,419,673 B1 | 7/2002 | Edwards et al. |
| 6,425,867 B1 | 7/2002 | Vaezy et al. |
| 6,432,067 B1 | 8/2002 | Martin et al. |
| 6,461,296 B1 | 10/2002 | Desai |
| 6,463,331 B1 | 10/2002 | Edwards |
| 6,482,203 B2 | 11/2002 | Paddock et al. |
| 6,485,413 B1 | 11/2002 | Boppart et al. |
| 6,506,154 B1 | 1/2003 | Ezion et al. |
| 6,506,156 B1 | 1/2003 | Jones et al. |
| 6,506,171 B1 | 1/2003 | Vitek et al. |
| 6,507,747 B1 | 1/2003 | Gowda et al. |
| 6,508,815 B1 | 1/2003 | Strul et al. |
| 6,522,142 B1 | 2/2003 | Freundlich |
| 6,540,677 B1 | 4/2003 | Angelsen et al. |
| 6,543,272 B1 | 4/2003 | Vitek |
| 6,550,482 B1 | 4/2003 | Burbank et al. |
| 6,554,780 B1 | 4/2003 | Sampson et al. |
| 6,554,801 B1 | 4/2003 | Steward et al. |
| 6,559,644 B2 | 5/2003 | Froundlich et al. |
| 6,569,159 B1 | 5/2003 | Edwards et al. |
| 6,579,298 B1 | 6/2003 | Bruneau et al. |
| 6,589,237 B2 | 7/2003 | Woloszko et al. |
| 6,602,251 B2 | 8/2003 | Burbank et al. |
| 6,610,054 B1 | 8/2003 | Edwards et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,623,481 B1 | 9/2003 | Garbagnati et al. |
| 6,626,854 B2 | 9/2003 | Friedman et al. |
| 6,626,855 B1 | 9/2003 | Weng et al. |
| 6,632,193 B1 | 10/2003 | Davison et al. |
| 6,635,055 B1 | 10/2003 | Cronin |
| 6,635,065 B2 | 10/2003 | Burbank et al. |
| 6,638,275 B1 | 10/2003 | McGaffigan et al. |
| 6,638,286 B1 | 10/2003 | Burbank et al. |
| 6,645,162 B2 | 11/2003 | Friedman et al. |
| 6,645,202 B1 | 11/2003 | Pless et al. |
| 6,652,516 B1 | 11/2003 | Gough |
| 6,660,002 B1 | 12/2003 | Edwards et al. |
| 6,660,024 B1 | 12/2003 | Flaherty et al. |
| 6,663,624 B2 | 12/2003 | Edwards et al. |
| 6,663,626 B2 | 12/2003 | Truckai et al. |
| 6,666,833 B1 | 12/2003 | Friedman et al. |
| 6,669,643 B1 | 12/2003 | Dubinsky |
| 6,679,855 B2 | 1/2004 | Horn et al. |
| 6,685,639 B1 | 2/2004 | Wang et al. |
| 6,689,128 B2 | 2/2004 | Sliwa et al. |
| 6,692,490 B1 | 2/2004 | Edwards |
| 6,701,931 B2 | 3/2004 | Sliwa et al. |
| 6,705,994 B2 | 3/2004 | Vortman et al. |
| 6,712,815 B2 | 3/2004 | Sampson et al. |
| 6,716,184 B2 | 4/2004 | Vaezy et al. |
| 6,719,755 B2 | 4/2004 | Sliwa et al. |
| 6,728,571 B1 | 4/2004 | Barbato |
| 6,730,081 B1 | 5/2004 | Desai |
| 6,735,461 B2 | 5/2004 | Vitek et al. |
| 6,743,184 B2 | 6/2004 | Sampson et al. |
| 6,746,447 B2 | 6/2004 | Davison et al. |
| 6,764,488 B1 | 7/2004 | Burbank et al. |
| 6,773,431 B2 | 8/2004 | Eggers et al. |
| 6,790,180 B2 | 9/2004 | Vitek |
| 6,805,128 B1 | 10/2004 | Pless et al. |
| 6,805,129 B1 | 10/2004 | Pless et al. |
| 6,813,520 B2 | 11/2004 | Truckai et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 * | 1/2005 | Lee ............ A61B 17/42 128/898 |

(56) References Cited

U.S. PATENT DOCUMENTS

| | | | |
|---|---|---|---|
| 6,899,712 B2 | 5/2005 | Moutafis et al. | |
| 6,921,398 B2 | 7/2005 | Carmel et al. | |
| 6,936,048 B2 | 8/2005 | Hurst | |
| 6,944,490 B1 | 9/2005 | Chow | |
| 6,969,354 B1 | 11/2005 | Marian | |
| 7,101,387 B2 * | 9/2006 | Garabedian | A61B 90/04 607/105 |
| 7,160,296 B2 | 1/2007 | Pearson et al. | |
| 7,229,401 B2 | 6/2007 | Kindlein | |
| 7,247,141 B2 | 7/2007 | Makin et al. | |
| 7,387,628 B1 | 6/2008 | Behl et al. | |
| 7,517,346 B2 | 4/2009 | Sloan et al. | |
| 7,963,941 B2 | 6/2011 | Wilk | |
| 8,080,009 B2 | 12/2011 | Lee et al. | |
| 8,157,741 B2 | 4/2012 | Hirota | |
| 8,157,745 B2 | 4/2012 | Schoot | |
| 8,216,231 B2 | 7/2012 | Behl et al. | |
| 8,221,321 B2 | 7/2012 | McMorrow et al. | |
| 8,262,574 B2 | 9/2012 | Placek et al. | |
| 8,287,485 B2 | 10/2012 | Kimura et al. | |
| 8,377,041 B2 | 2/2013 | Frassica et al. | |
| 8,469,893 B2 | 6/2013 | Chiang et al. | |
| 8,512,330 B2 | 8/2013 | Epstein et al. | |
| 8,512,333 B2 | 8/2013 | Epstein et al. | |
| 8,540,634 B2 | 9/2013 | Bruce et al. | |
| 8,585,598 B2 | 11/2013 | Razzaque et al. | |
| 8,622,911 B2 | 1/2014 | Hossack et al. | |
| 8,663,130 B2 | 3/2014 | Neubach et al. | |
| 8,718,339 B2 | 5/2014 | Tonomura et al. | |
| 8,814,796 B2 | 8/2014 | Martin et al. | |
| 9,089,287 B2 | 7/2015 | Sliwa et al. | |
| 9,198,707 B2 | 12/2015 | McKay et al. | |
| 9,198,719 B2 | 12/2015 | Murdeshwar et al. | |
| 9,247,925 B2 | 2/2016 | Havel et al. | |
| 9,357,977 B2 | 6/2016 | Grossman | |
| 9,439,627 B2 | 9/2016 | Case et al. | |
| 9,510,898 B2 | 12/2016 | Epstein et al. | |
| 9,516,996 B2 | 12/2016 | Diolaiti et al. | |
| 10,321,951 B2 | 6/2019 | Placek et al. | |
| 2001/0014805 A1 | 8/2001 | Burbank et al. | |
| 2001/0051802 A1 | 12/2001 | Woloszko et al. | |
| 2002/0022835 A1 | 2/2002 | Lee | |
| 2002/0052600 A1 | 5/2002 | Davison et al. | |
| 2002/0068871 A1 | 6/2002 | Mendlein et al. | |
| 2002/0077550 A1 | 6/2002 | Rabiner et al. | |
| 2002/0183735 A1 | 12/2002 | Edwards et al. | |
| 2003/0009164 A1 | 1/2003 | Woloszko et al. | |
| 2003/0014046 A1 | 1/2003 | Edwards et al. | |
| 2003/0028111 A1 | 2/2003 | Vaezy et al. | |
| 2003/0032896 A1 | 2/2003 | Bosley et al. | |
| 2003/0114732 A1 | 6/2003 | Webler et al. | |
| 2003/0130575 A1 | 7/2003 | Desai | |
| 2003/0130655 A1 | 7/2003 | Woloszko et al. | |
| 2003/0195420 A1 | 10/2003 | Mendlein et al. | |
| 2003/0195496 A1 | 10/2003 | Maguire et al. | |
| 2003/0199472 A1 | 10/2003 | Al-Hendy et al. | |
| 2003/0216725 A1 | 11/2003 | Woloszko et al. | |
| 2003/0216759 A1 | 11/2003 | Burbank et al. | |
| 2004/0002699 A1 | 1/2004 | Ryan et al. | |
| 2004/0030268 A1 | 2/2004 | Weng et al. | |
| 2004/0054366 A1 | 3/2004 | Davison et al. | |
| 2004/0120668 A1 | 6/2004 | Loeb | |
| 2004/0143252 A1 | 7/2004 | Hurst | |
| 2004/0153057 A1 | 8/2004 | Davison | |
| 2004/0175399 A1 | 9/2004 | Schiffman et al. | |
| 2004/0176760 A1 | 9/2004 | Qiu | |
| 2004/0193028 A1 | 9/2004 | Jones et al. | |
| 2004/0215182 A1 | 10/2004 | Lee | |
| 2004/0230190 A1 | 11/2004 | Dahla et al. | |
| 2004/0254572 A1 | 12/2004 | McIntyre et al. | |
| 2005/0038340 A1 | 2/2005 | Vaezy et al. | |
| 2005/0107781 A1 | 5/2005 | Ostrovsky et al. | |
| 2005/0124882 A1 | 6/2005 | Ladabaum et al. | |
| 2005/0149013 A1 | 7/2005 | Lee | |
| 2005/0197577 A1 | 9/2005 | Makin et al. | |
| 2005/0215990 A1 | 9/2005 | Govari | |
| 2005/0216039 A1 | 9/2005 | Lederman | |
| 2005/0228288 A1 | 10/2005 | Hurst | |
| 2005/0255039 A1 | 11/2005 | Desai | |
| 2005/0256405 A1 | 11/2005 | Makin et al. | |
| 2006/0010207 A1 | 1/2006 | Akerman et al. | |
| 2006/0058680 A1 | 3/2006 | Solomon | |
| 2006/0178665 A1 * | 8/2006 | Sloan | A61B 18/1477 606/41 |
| 2006/0184049 A1 | 8/2006 | Tsujita | |
| 2006/0189972 A1 * | 8/2006 | Grossman | A61B 18/1477 606/41 |
| 2007/0006215 A1 * | 1/2007 | Epstein | A61B 18/1477 717/171 |
| 2007/0016183 A1 | 1/2007 | Lee et al. | |
| 2007/0083082 A1 | 4/2007 | Kiser et al. | |
| 2007/0112306 A1 * | 5/2007 | Agnew | A61M 25/0021 604/164.13 |
| 2007/0249936 A1 * | 10/2007 | Deckman | A61B 8/445 600/458 |
| 2007/0249939 A1 | 10/2007 | Gerbi et al. | |
| 2008/0033493 A1 | 2/2008 | Deckman et al. | |
| 2008/0188916 A1 | 8/2008 | Jones et al. | |
| 2008/0228081 A1 | 9/2008 | Becker et al. | |
| 2009/0043295 A1 | 2/2009 | Arnal et al. | |
| 2010/0222677 A1 | 9/2010 | Placek et al. | |
| 2010/0262133 A1 | 10/2010 | Hoey et al. | |
| 2012/0165813 A1 | 6/2012 | Lee et al. | |
| 2012/0209115 A1 | 8/2012 | Tonomura | |
| 2012/0277737 A1 | 11/2012 | Curley | |
| 2013/0281863 A1 | 10/2013 | Chiang et al. | |
| 2013/0317366 A1 | 11/2013 | Hirayama et al. | |
| 2014/0180273 A1 | 6/2014 | Nair | |
| 2014/0276081 A1 | 9/2014 | Tegels | |
| 2015/0150497 A1 | 6/2015 | Goldchmit | |
| 2015/0173592 A1 | 6/2015 | Leeflang et al. | |
| 2015/0257779 A1 | 9/2015 | Sinelnikov et al. | |
| 2016/0151041 A1 | 6/2016 | Lee et al. | |
| 2016/0278740 A1 | 9/2016 | Negrila et al. | |
| 2016/0310042 A1 | 10/2016 | Kesten et al. | |

FOREIGN PATENT DOCUMENTS

| | | |
|---|---|---|
| WO | WO-9814169 A1 | 4/1998 |
| WO | WO-9943366 A1 | 9/1999 |
| WO | WO-0000098 A1 | 1/2000 |
| WO | WO-0180723 A2 | 11/2001 |
| WO | WO-0195819 A1 | 12/2001 |
| WO | WO-0211639 A1 | 2/2002 |
| WO | WO-0180723 A3 | 4/2002 |
| WO | WO-03005882 A2 | 1/2003 |
| WO | WO-03065908 A1 | 8/2003 |
| WO | WO-03005882 A3 | 11/2003 |
| WO | WO-2004002293 A2 | 1/2004 |
| WO | WO-2004002550 A2 | 1/2004 |
| WO | WO-2004020011 A1 | 3/2004 |
| WO | WO-2004035110 A2 | 4/2004 |
| WO | WO-2004035110 A3 | 6/2004 |
| WO | WO-2004058328 A2 | 7/2004 |
| WO | WO-2004064658 A1 | 8/2004 |
| WO | WO-2004002550 A3 | 10/2004 |
| WO | WO-2004058328 A3 | 10/2004 |
| WO | WO-2004002293 A3 | 7/2005 |
| WO | WO-2007005830 A2 | 1/2007 |
| WO | WO-2007144004 A1 | 12/2007 |

OTHER PUBLICATIONS

Bergamini, et al. Laparoscopic Radiofrequency Thermal Ablation: A New Approach to Symptomatic Uterine Myomas. Am. J. Obstetrics and Gynecology (2005) 192: 768-73.

CNN.com Health Women. Experimental technique uses lasers to shrink uterine fibroids. Nov. 28, 2000.

European search report and search opinion dated Jul. 28, 2015 for EP Application No. 15163596.8.

European search report dated Jul. 6, 2012 for EP Application No. 10746938.9.

(56) References Cited

OTHER PUBLICATIONS

Hindley, et al. MRI guidance of focused ultrasound therapy of uterine fibroids: Early results. American Journal of Roentgenology, 2004, 183(6): 1173-1719.
International search report and written opinion dated Apr. 26, 2010 for PCT/US2010/025647.
Kanaoka, et al. Microwave endometrial ablation at a frequency of 2.45 Ghz. A pilot study. J Reprod Med. Jun. 2001; 46(60): 559-63.
Law, et al. Magnetic resonance-guided percutaneous laser ablation of uterine fibroids. J Magn Reson Imaging, Oct. 2000; 12(4):565-70.
Liu, et al. Catheter-Based Intraluminal Sonography. J. Ultrasound Med., 2004, 23:145-160.
Mogami, et al. Usefulness of MR-guided percutaneous cryotherapy. Med. Imaging Technol. 2004, 22(3): 131-6. (English abstract).
MSNBC Online Articles, About US: Articles; "Intrauerine Fibroids Can Now Be Treated Nonsurgically" http://www.fibroids.com/news-blog/2004/08/intrauterine-fibroids-can-now-be-treated-nonsurgically/ Aug. 23, 2004.
Notice of allowance dated Jun. 7, 2012 for U.S. Appl. No. 12/712,969.
Office action dated Feb. 1, 2012 for U.S. Appl. No. 12/712.969.
Office Action dated Feb. 1, 2017 for U.S. Appl. No. 13/589,956.
Office action dated Apr. 9, 2015 for U.S. Appl. No. 13/589,956.
Office action dated Dec. 26, 2014 for U.S. Appl. No. 13/589,956.
Okamura, et al. Force Modeling for Needle Insertion into Soft Tissue. IEEE Transactions on Biomedical Engineering, Oct. 2001, 10 (51): 1707-1716.
RSNA 2000 Explore News Release. Lasers Liquefy Uterine Fibroid Tumors. 11:30 a.m. CST, Monday, Nov. 27, 2000.
Senoh, et al. Saline Infusion Contrast Intrauterine Sonographic Assessment of the Endometrium with High-Frequency, Real-Time Miniature Transducer Normal Menstrual Cycle: a Preliminary Report. Human Reproduction, 14 (10): 2600-2603, 1999.
Vascular and Interventional Radiology, SRSC; Nonsurgical Treatment of Uterine Fibroids. Available at http://www.drfibroid.com/treatment.htm. Accessed Apr. 11, 2011.
Websand, Inc., New treatment options for fibroid tumors, Copyright 2002 by WebSand, Inc.
U.S. Appl. No. 13/589,956 Office Action dated Apr. 7, 2016.
U.S. Appl. No. 13/589,956 Notice of Allowance dated Feb. 5, 2019.

\* cited by examiner

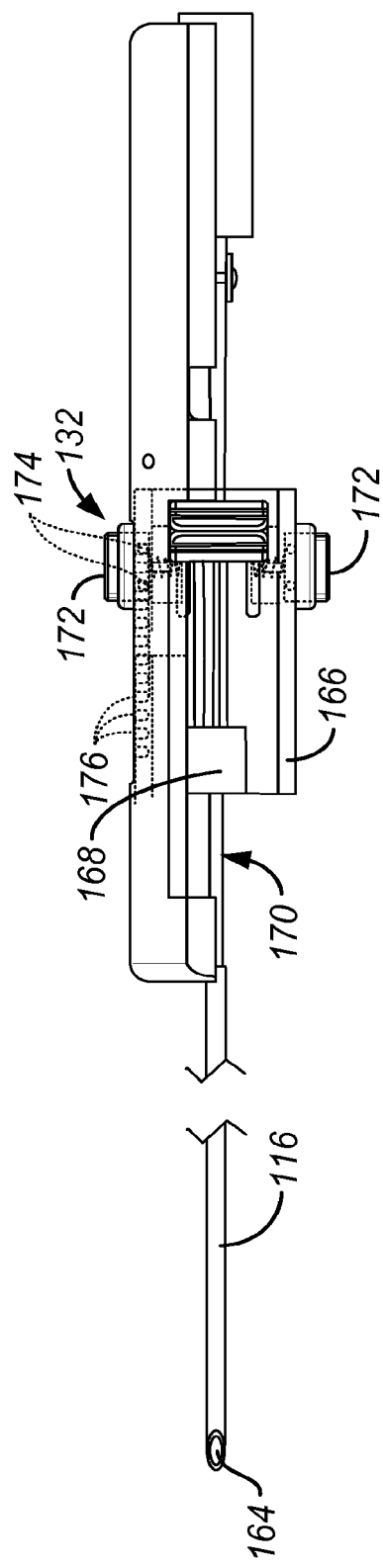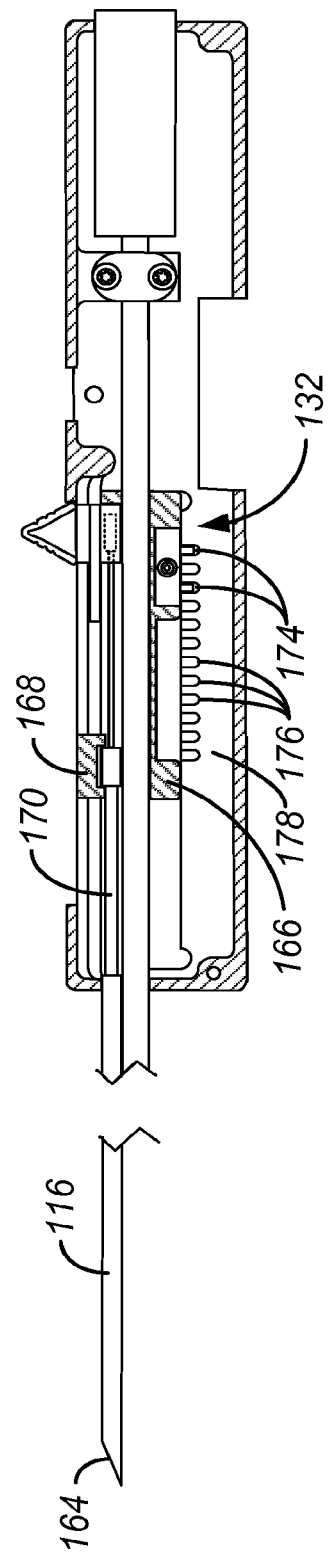

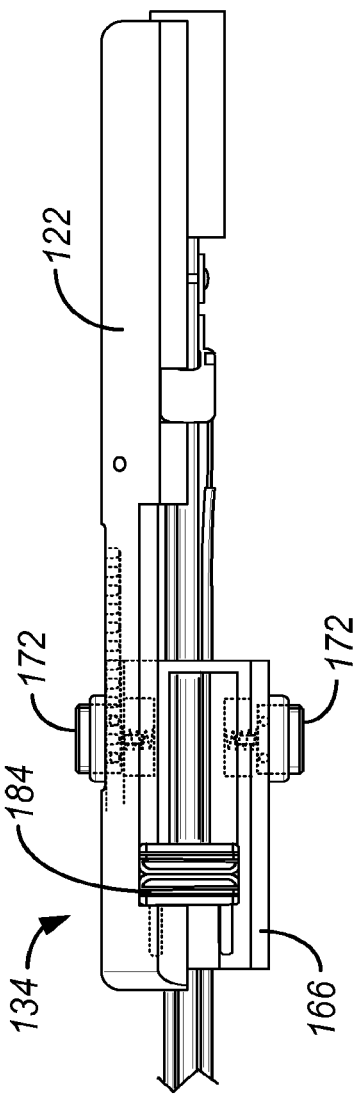
FIG. 13
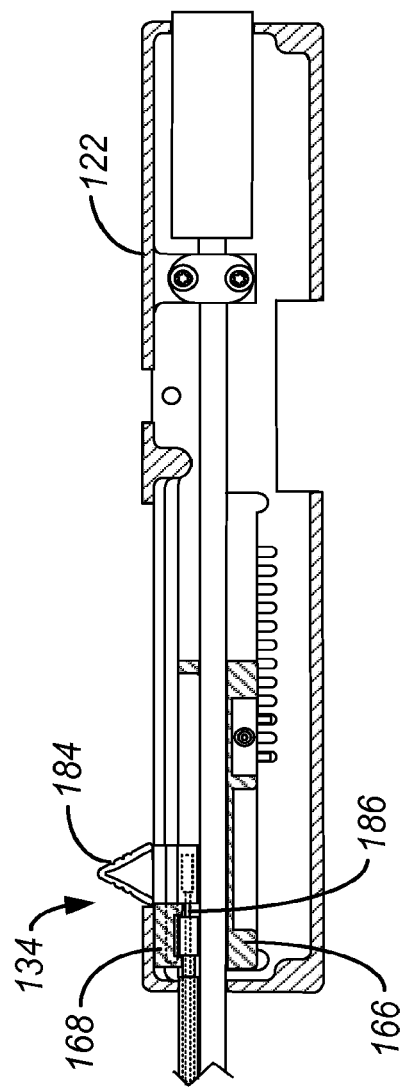
FIG. 14
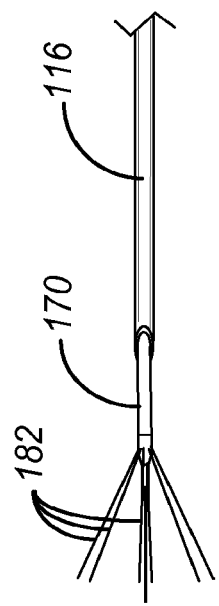

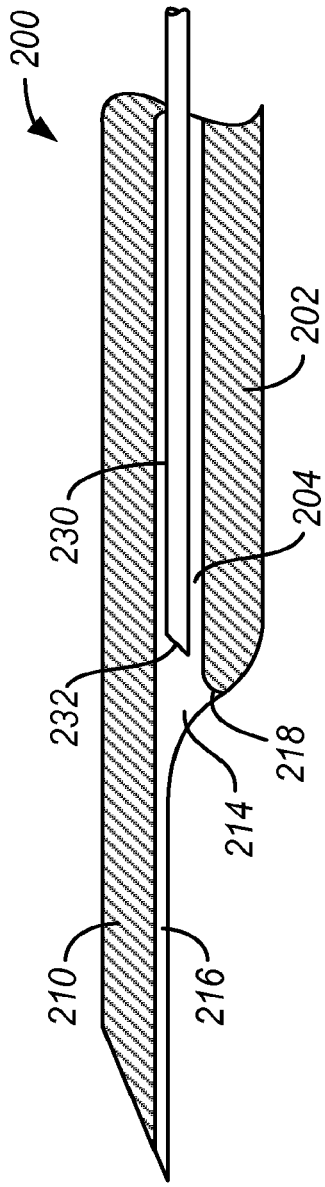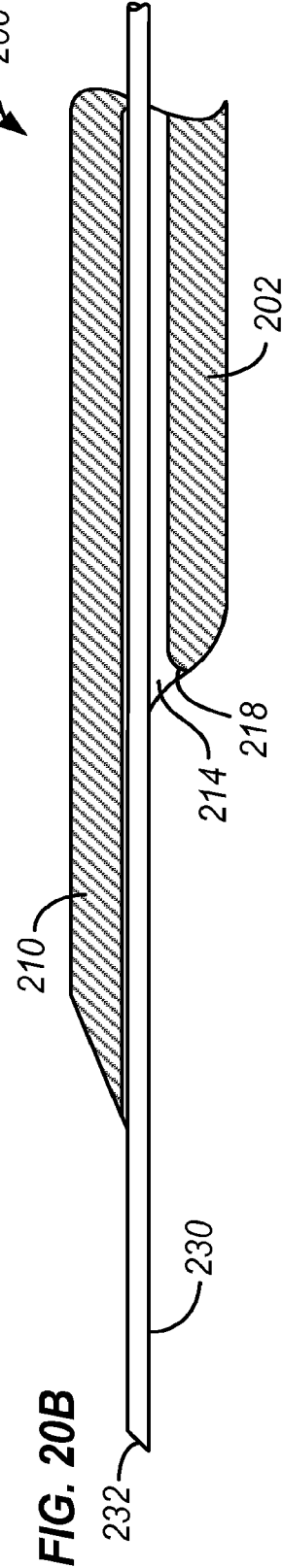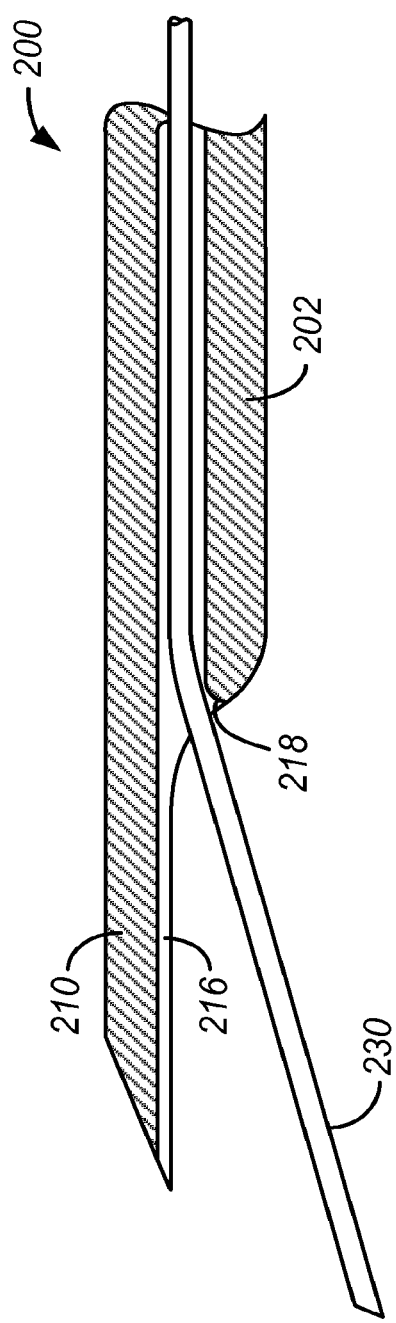

NEEDLE AND FINE DEPLOYMENT MECHANISM

CROSS-REFERENCE TO RELATED APPLICATION

The present application is a continuation of U.S. patent application Ser. No. 13/589,956, filed Aug. 20, 2012, now U.S. Pat. No. 10,321,951; which is a divisional of Ser. No. 12/712,969, filed Feb. 25, 2010, now U.S. Pat. No. 8,262,574; which claims the benefit of provisional application No. 61/156,270, filed on Feb. 27, 2009 the full disclosures of which are incorporated herein by reference.

BACKGROUND OF THE INVENTION

1. Field of the Invention

The present invention relates generally to medical devices and methods. More particularly, the present invention relates to a therapy device having a deployable treatment needle with a plurality of tines deployable in a straight path from said needle.

Uterine fibroids are benign tumors in the uterine wall and are the most common tumor of the female pelvis. Fibroids afflict up to 30% of women of childbearing age and can cause significant symptoms including discomfort, pelvic pain, mennorhagia (excessive bleeding), anemia, infertility, and miscarriage. While fibroids may be located in the muscle (intramural), adjacent to the endometrium (submucosal), or in the outer layer of the uterus (subserosal), and can grow up to several centimeters in diameter.

Current treatments for fibroids include both pharmaceutical and surgical intervention. Pharmaceutical treatments include the administration of NSAIDS, estrogen-progesterone combinations, and the like. Medications, however, are generally ineffective and are palliative rather than curative. Surgical interventions include myomectomy, where fibroids are removed in an open surgical procedure requiring laparotomy and general anesthesia, and hysterectomy, involving complete surgical removal of the uterus. Both these procedures are long and have significant blood loss.

As improvements over open surgical procedures, several minimally invasive procedures have been developed. Laparoscopic myomectomy is a laparoscopic procedure requiring highly skilled laparoscopic gynecologists. Uterine artery embolization relies on blocking the uterine artery supplying blood to the fibroid by injecting small particles. While sometimes effective, common complications of arterial embolization include infection, premature menopause, and severe pelvic pain. A third approach relies on complete endometrial ablation, which is generally effective for treating bleeding but less reliable for treating fibroids.

More recently, and of particular interest to the present invention, the use of radiofrequency needles and other ablation elements for treating individual fibroids via a transvaginal approach has been proposed. As described, for example, in published U.S. Patent Applications 2006/0189972; 2007/0179380; 2007/0249936; and 2008/0033493, each of which is commonly assigned with the present application, a probe carrying a needle is used to treat individual fibroids. The probe carries on-board ultrasonic or other imaging so that the needle can be guided into the fibroid under direct observation.

While effective in many cases, the use of a single needle for treating fibroids and other solid tissue masses has certain shortcomings. In particular, the volume of tissue that can be treated by a single needle is limited. Even if large diameter needles are used, the surface area of the needle limits the amount of energy that can be imparted into the tissue and ultimately limits the distance from the needle that can be effectively treated.

To increase the effective volume that can be treated using a single needle deployment, the use of multiple, simultaneously deployed needles has been proposed. Of particular pertinence, U.S. Pat. No. 6,050,992 describes a system for deploying multiple everting needles from a single central cannula. In some instances, the needles can be deployed over an outwardly curving surface (see FIG. 9). The needles, however, are generally intended to be pre-shaped so that they evert outwardly, as shown in FIG. 16. U.S. Patent Publication No. 2007/0006215 also describes a needle having multiple stylets which are outwardly deployed over outwardly curving ramps. Because of the limited diameter of the central needle, the ramps must be relatively steep and cover a relatively short distance to gain the desired outward deflection. The use of such short, relatively steep ramps can impart excessive stress to the needles being deployed, particularly if the needles are not pre-shaped in their outwardly curved configuration.

For these reasons, it would be desirable to provide needle structures and deployment assemblies capable of deploying multiple needles, tines, or other components in order to increase the volume of tissue to which radiofrequency or other electrical energy can be delivered. It would be further desirable to provide such multiple needle delivery structures and deployment assemblies where the diameter, width, length, and other dimensions of the structure may be minimized. It would be still further desirable to provide such multiple needle deployment structures and deployment assemblies which have a reduced or minimized insertion force for advancement through solid tissue. It would be additionally desirable to provide a needle delivery structure in which placement of the needle or electrode is predictable. At least some of these objectives will be met by the inventions described hereinbelow.

2. Brief Description of the Background Art

The following US published applications discussed above are relevant to the present invention: 2006/0189972; 2007/0179380; 2007/0249936; and 2008/0033493. The disclosures of each of these applications is incorporated herein by reference. See also U.S. Pat. No. 6,050,992 and US 2007/0006215.

BRIEF SUMMARY OF THE INVENTION

In a first aspect of the present invention, a needle electrode deployment shaft comprises a central member and a plurality of needle electrodes which are deployable from the central member. The central member will have a proximal end, a distal end, a longitudinal axis therebetween, an outer surface, and a plurality of needle electrode advancement channels therein, typically formed in the outer surface. Each channel will have an axially aligned proximal portion and an outwardly directed distal ramp portion such that as the needle electrodes are advanced through the channel, the needles will be deflected radially outwardly as they pass over the ramp so that they can enter the tissue in an outwardly diverging pattern. The ramp may be flat or curved, but will usually be curved as described in more detail below.

The individual needles may be elastic or malleable, where suitable malleable needles are formed from stainless steel, titanium, or tungsten, gold, silver, or other conventional malleable metals. Suitable elastic needles may be formed from spring stainless steels, shape memory alloys, such as nitinol, eligiloy, and the like. In preferred aspects, the needles will be elastic with a pre-shaped straight configuration so that the portion of the needle passing over the ramp will be reversibly deflected with the portion of the needle distal to the ramp returning back to a straight configuration. It is desirable to minimize residual strain after multiple deflection or bending cycles. Residual strain can be minimized by ensuring the electrode material is not appreciably stressed beyond its elastic limit. This allows for repeatable needle electrode placements, and, thus, repeatable treatment ablation volumes.

It will generally be desirable to deflect the advancing needles outwardly at a relatively large angle, typically from 20.degree. to 50.degree., preferably 25.degree. to 45.degree., relative to the axis of the central member, more preferably an angle such that the tissue is adequately ablated. While such angles of deflection could theoretically be obtained by providing relatively short, sharply angled ramps, such short, steeply deflected ramps will increase the stress imparted to the needles. By increasing the radial component of the lengths of the ramps, the exit angle of the needles relative to the axis of the central member is increased for a given stress level. The ability to increase the exit angle, for example, by lengthening the ramp, however, can be limited in certain designs, particularly designs having a relatively small diameter central member.

Therefore, in accordance with the principles of the present invention, ramps may be provided in the channels formed in the central member where the entrance to and exit from the ramp are angularly offset from each other. That is, the ramp entrance will be located at a first angular orientation relative to the longitudinal axis and at a pre-selected depth beneath the outer surface and the ramp exit will be located at a second angular orientation which is angularly offset from the first angular orientation. By angularly offsetting the entrance and exit of the ramp, the length of the ramp (including the radial component) through which the needle electrodes travel will be increased. By increasing the radial component of the ramp length, the stress imparted into individual needles can remain in the desired elastic strain limit while allowing a larger exit angle. By so doing, the needles may be deployed multiple times with predictable deployment placement.

The central member may be formed of a simple tube or cannula, but will more usually have a sharpened distal end which allows the central member to self-penetrate into tissue prior to deployment of the needle electrodes. The central member may be electrically passive or neutral (so that it does not itself act as an electrode) or may be electrically active, either being connected with the same (monopolar) or the opposite (bipolar) polarity as individual needle electrode (s). The individual needle electrodes may also be connected with a common polarity or different polarities, allowing for a variety of specific monopolar and bipolar needle configurations to be utilized. The needle electrode deployment shafts of the present invention will usually have from three to nine channels and from three to nine electrodes, preferably one electrode in each channel. The angular offset between the first angular orientation of the ramp entrance and second angular orientation of the ramp exit will preferably be in the range from 0.degree. to 180.degree., more preferably 45.degree. to 150.degree. The central member will typically have a diameter in the range from 0.75 mm to 3.1 mm and the pre-selected radial distance at the ramp entrance will be in the range from 0.25 mm to 1.25 mm. The axial distance between the ramp entrance and the ramp exit will usually be in the range from 2.5 mm to 25 mm.

As described above, the ramp entrance and the ramp exit will be angularly offset from one another, where such angular offset increases the distance between the entrance and exit relative to the distance if the entrance and exit had been axially aligned. The path between the angularly offset entrance and exit may itself be straight, but will more usually be curved, sometimes following a generally spiral pattern, as will be described in greater detail in connection with the drawings hereinafter.

The needle electrodes may have a variety of tip configurations, but will usually have a sharpened or other tip which is configured to permit self-penetration of the needle electrodes as they are advanced from the central member. In a preferred configuration, the needle electrodes will have a beveled end with a surface which is oriented so that it engages a surface of the ramp as the needle is advanced through the channel. The beveled end will thus reduce the friction and seizing which could occur if a sharpened edge of the needle were to be engaged against the ramp as the needle is advanced. The surface may be flat (planar), curved, multi-faceted, or otherwise configured to engage the ramp with minimum friction.

In another aspect of the present invention, the needle electrode deployment shafts and assemblies just described may be incorporated into a probe body, optionally together with an ultrasonic imaging array, in order to provide an imaging and therapeutic delivery system. The probe body will typically be able to penetrate solid tissue (usually having a self-penetrating tip and/or a passage for receiving a stylet), allowing deployment of both the needle electrodes and the ultrasonic imaging array from the probe body to treat fibroids or other tissue masses within solid tissue. Usually, the ultrasonic imaging array will be configured and positioned so that deployment of the needle electrodes from the deployment shaft may be monitored.

In a further aspect of the apparatus of the present invention, a needle electrode deployment shaft comprises a central member and a plurality of needle electrodes deployable from the central member. The central member has a proximal end, a distal end, a longitudinal axis therebetween, an outer surface, and a plurality of needle electrode advancement channels therein. Each channel has an axially aligned proximal portion and an outwardly directed distal portion.

In specific accordance with the present invention, the needle electrode deployment shafts may include a spike or other introducer tip having a sharpened tip which extends from the distal end of the central member. The spike will have a diameter which is less than that of the central member, typically being in a range from 20% to 95% of the diameter of the central member, preferably for 25% to 60%, and more preferably from 30% to 55%, where the reduced diameter spike reduces the insertion force required to advance the shaft into tissue (prior to subsequent deployment of the needle electrodes from the shaft). Such needle electrode deployment shafts will preferably further comprise a transition region between the spike and the central member, where the transition region may be conical, spherical, or have other geometric configurations. In some cases, the transition region may define a cutting edge to further facilitate advancement of the shaft into solid tissue.

In a still further aspect of the present invention, methods for treating uterine fibroids comprise introducing a probe into a uterus. An ultrasonic transducer carried by the probe is used to locate the uterine fibroid or other tissue mass to be treated. A needle deployment shaft is advanced from the probe in the uterine tissue proximate the uterine fibroid, and a plurality of needle electrodes are advanced from the deployment shaft into the uterine fibroid and/or tissue surrounding the uterine fibroid. The needles are advanced through an array of outwardly directed channels or ramps into the uterine fibroid and/or tissue surrounding the uterine fibroid, and energy is delivered from the needle electrodes to necrose the fibroid. Typically, the energy is radiofrequency energy, where the radiofrequency energy may be monopolar or bipolar.

In a further aspect of the present invention, a needle electrode deployment device comprises a central member having a proximal end, a distal end, and a pre-defined cross-sectional area. The central member will typically be cylindrical, and the cross-sectional area will be the area of the circular cross-section normal to the axis of the cylindrical central member. Other, non-circular cross sections may also be employed, and in certain cases, the central member could be tapered, typically with a reduced cross-sectional area nearer its distal end.

The needle electrode deployment device may further comprise a central electrode or needle having a tissue-penetrating distal end which is slidably received in an axially aligned central electrode advancement lumen or passage formed through the central member, usually extending fully from the proximal end to the distal end and terminating in an open electrode deployment port at the distal end. The device further comprises a spike or introducer tip extending distally from the distal end of the central member, where the spike has a cross-sectional area which is less than that of the central member, typically being less than one half of the cross-sectional area of the central member, typically being no more than 45% of the central member area, and more typically being no more than 40% of the central member area. The cross-sectional geometry of the spike or introducer tip may vary, but in all instances there will be a tissue-penetrating element or geometry provided at the distal end thereof. In the exemplary embodiments, the tissue-penetrating distal end is in the form of a sharpened, typically trocar-style tip so that the spike can be advanced into solid tissue followed by the central member. The tissue-penetrating spike will also have an axis, and in certain embodiments the axis of the spike will be parallel to but radially offset from the axis of the central member, typically having a radially outer surface aligned with the radially outer surface of the central member. The radially offset orientation of the spike or other introducer tip opens and provides access to the distal electrode deployment port of the electrode advancement passage so that the needle electrode can be axially advanced from the central member to follow a path which is parallel to that of the spike or other introducer tip.

Positioning of the introducer tip in "offset alignment" with the tissue-penetration path of the needle being advanced from the electrode advancement passage is advantageous since it reduces focal stress on the electrode by having its electrode advancement passage exit more proximal than the most distal portion of the introducer tip. After the device has been introduced into tissue, the central electrode can sometimes become misaligned due to movement of the device by the physician. By having the electrode deployment passage exit more proximal, the focal stress induced on the electrode by the introducer tip during retraction is reduced thereby facilitating retraction of the needle back into the passage. In the prior embodiments, such as those shown in FIGS. 4A-4C, an electrode which extends through the port 185 can be bent and stressed at the point where it exits the port particularly during retraction. Bending at this transition can make retraction of the needle more difficult and cause permanent deformation of the electrode. In the embodiments where the needle is extended in parallel and radially offset to the introducer tip, the chance of such electrode needle deformation and binding is substantially reduced.

In the exemplary embodiments, the introducer tip will be joined to the central member by a transition region, usually a region which tapers in the distal direction from the distal end of the central member toward the proximal end of the introducer tip, e.g. a conical transition zone. This tapered or conical transition region facilitates advancement of the central member into tissue following the initial introduction of the introducer tip. In other exemplary aspects of the present invention, the introducer tip may have an axial channel in the surface which is disposed alongside the needle advancement path. Thus, the needle may be advanced through the channel to further enhance stabilization of the needle. In a still further exemplary aspect of the needle electrode deployment device, an exit port of the electrode advancement passage will have a rounded peripheral edge to still further decrease focal stress and the chance of binding and damage to the needle as the needle is retracted back within the electrode advancement passage. Finally, while the needle electrode deployment device may be used with only a single central needle, as described thus far, usually it will be combined with a plurality of laterally deployable needle electrodes as described in conjunction with the previous embodiments of the present invention.

In addition to the radially offset spike just described the spike or other introducer tip of the present invention may take a variety of other forms. For example, the spike may have a chamfered surface which provides a tapered profile extending from the distal end of the central member to the distal tip of the spike or introducer tip. The chamfered surface will have an opening or port which allows advancement of the central electrode therethrough. Usually, the port or opening will comprise an electrode transition cavity which can have a generally spherical, conical, or ovoid shape which extends from the electrode deployment port of the central lumen in the central member. The electrode deployment port itself may be in the form of a slot, circle, oval, or have a variety of other configurations.

In a further embodiment, the introducer tip may comprise a plurality of axially aligned spikes extending from the distal end of the central member, typically from the periphery of the distal end. In this way, the central electrode may be advanced distally through a protected region defined within the plurality of spikes.

Finally, in a further embodiment, the introducer tip or spike may be solid and fixedly attached to the distal end of the central member. By electrically isolating a portion of the fixed spike, the spike may act as a central electrode and replace the axially reciprocated central electrode of the other embodiments described herein.

The various embodiments described above significantly increase the number of times that the needle electrode deployment device may be used in a single procedure on a patient. Repeated deployment of the central electrode can often cause undue stress and wear, often resulting from interference and interaction with the exit port from the central electrode lumen or passageway, both as the central electrode is deployed and refracted as well as when the device is angled and manipulated in tissue during use. The particular needle exit configurations described above can lessen the stress and increase the deployable electrode life. In the case of the fixed center electrode, the requirement of repeated center electrode deployment is eliminated altogether.

BRIEF DESCRIPTION OF THE DRAWINGS

FIGS. 9-14 illustrate the mechanisms which are used to deploy the needle electrode deployment shaft and needle electrodes as part of the probe.

FIGS. 20A-20C are schematic illustrations showing the advancement of the needle electrode from a centrally aligned electrode advancement passage within the needle electrode deployment device of FIGS. 17-19.

DETAILED DESCRIPTION OF THE INVENTION

Figure 1:
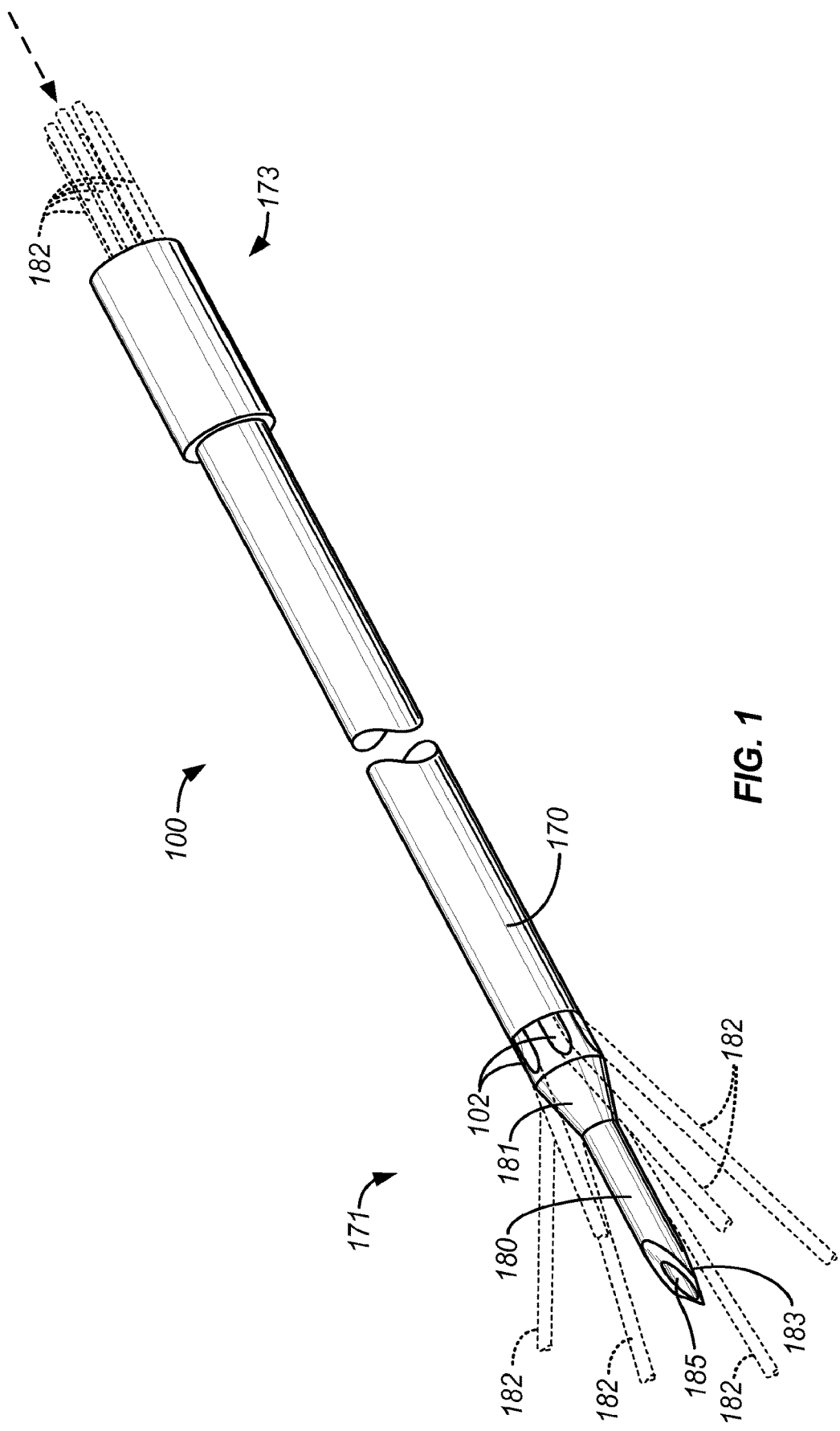
FIG. 1 is a perspective view of a needle electrode deployment shaft constructed in accordance with the principles of the present invention.

The present invention provides electrode deployment structures comprising needle electrode deployment shafts capable of reciprocatably deploying a plurality of needle electrodes into solid tissue. The needle electrode deployment shafts will comprise a central member having a proximal end, a distal end, and a longitudinal axis therebetween. Typically, the central member will have a distal end which is configured to permit self-penetration, e.g. the central member may itself be a needle having a sharpened or chamfered tip which permits the central member to be advanced into tissue by simply pushing. In other embodiments, the central member could comprise a hollow tubular body, commonly referred to as a cannula, having a needle or stylet removably received within a central lumen thereof. The cannula could then be introduced by placing the stylet with its sharpened tip extending from the distal end of the cannula and pushing the assembly of the cannula and stylet into tissue. The stylet could then be removed, leaving the lumen in place for other purposes. In a further alternative, the central member could have a tip with an electrode, optical element, abrasive surface, or otherwise configured to permit energy-mediated advancement of the distal tip through tissue.

The needle electrodes will typically be hollow core needles, tubes, or wires which have sufficient column strength so that they may be pushed from the central member into tissue. Typically, the needle electrodes will have sharpened tips but alternatively they could be configured with electrodes or other elements to permit energy-mediated advancement. The needle electrodes will typically be pre-shaped in a straight configuration but in other embodiments could be pre-shaped curved, helical, or have other geometries. The needle electrodes will also usually be elastic, typically being formed from an elastic metal, such as spring stainless steel, nitinol, eligiloy, or other superelastic material. By "pre-shaped" it is meant that the needles have an elastic memory of the desired straight or other configuration. In other embodiments, however, the needle electrodes could be formed from a malleable metal, such as various surgical steels where the needle electrodes may undergo plastic deformation as they are advanced over the ramp portion of the channel as described below.

The needle deployment shaft will usually be intended for deploying the plurality of needles into tissue in order to deliver radiofrequency or other electrical energy for treating the tissue. Treatments will usually comprise heating, more usually comprising the delivery of radiofrequency energy into the tissue via a monopolar or bipolar protocol. By monopolar, it is meant that the plurality of needle electrodes and optionally the central member will be connected to one pole of a radiofrequency generator while the other pole will be connected to a neutral or common electrode which is attached to the patient via a pad or other relatively large area electrical contact surface. By bipolar it is meant that at least some of the plurality of needle electrodes and/or the central member are connected to opposite poles of the radiofrequency power supply so that the radiofrequency current is concentrated between the oppositely connected electrodes and/or central member.

The needle electrode deployment shaft is particularly suitable for deploying the plurality of needles in solid tissues, such as uterine tissue, breast tissue, liver tissue, fibrous tissue, kidney tissue, pancreatic tissue, prostate tissue, brain tissue, skeletal muscle, and the like, for the delivery of energy to ablate tumors and other diseased portions of the tissue. In other instances, however, the needle electrode deployment shafts could be useful for deploying the plurality of needles for aesthetic treatments, such as collagen tightening, fat (adipose) tissue treatment, and the like.

Figure 2:
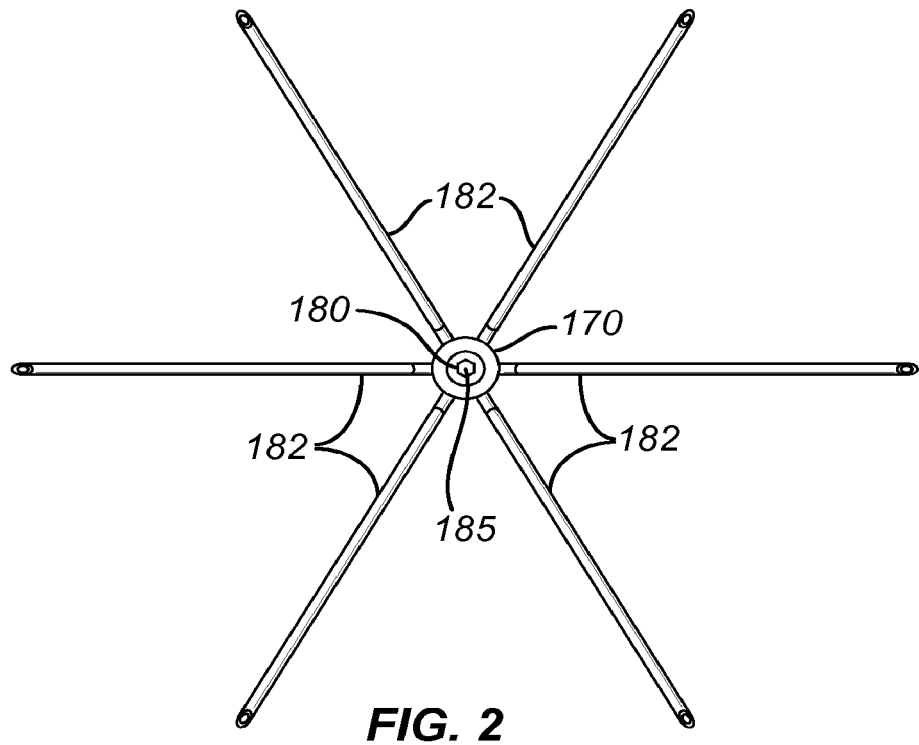
FIG. 2 is an end view of the needle electrode deployment shaft of FIG. 1 shown with the needle electrodes fully deployed.
Figure 3:
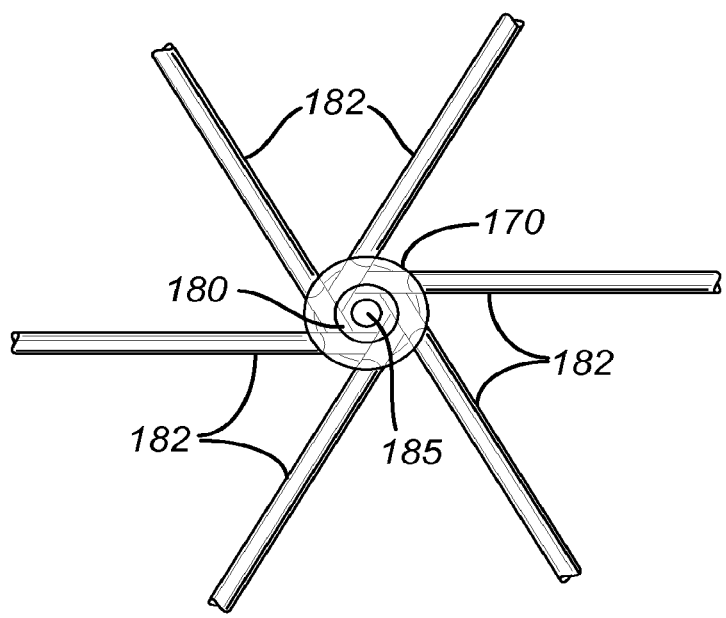
FIG. 3 is an alternative end view of the needle electrode deployment shaft of FIG. 1 shown with the plurality of needle electrodes deployed through angularly offset deployment ramps.

Referring now to FIG. 1, a needle electrode deployment structure 100 constructed in accordance with the principles of the present invention comprises a central member or main needle shaft 170 having a distal end 171 and a proximal end 173. The central member 170 includes a plurality of needle electrode advancement channels 102 which may each slidably receive a needle electrode 182, shown in broken line. The needle electrodes 182 may be axially advanced and retracted within the advancement channels 102 from a non-deployed configuration where they lie entirely within the channels to a deployed configuration where they extend radially outwardly from a central axis of the central member 170, as shown in FIGS. 2 and 3.

In one specific aspect of the invention, the central member or main needle shaft 170 has a tip 180 which has a reduced diameter relative to the proximal portions of the central member. In particular, the tip 180 is disposed coaxially along the same axis as the remainder of the central member 170 but is stepped-down in diameter, typically over a conical transition region 181. The tip 180 will terminate in a sharpened distal end 183 which is configured to facilitate advancement of the central member through tissue. Optionally, the entire central member 170 may have a central lumen or passage therethrough with a distal opening 185 illustrated in FIGS. 1-3.

The structure of tip 180 is advantageous since it reduces the insertion force required to advance the central member 170 through tissue. It will be appreciated that the smaller diameter of the tip 180 will require less force to be introduced into the tissue and will prepare a pilot tract through the tissue. The larger diameter proximal portion of the central member 170 may enter the established tissue tract with the force of entry being reduced by the conical transition region 181. By providing a proximal portion of the central member with a larger diameter, there is increased area and volume for forming the needle advancement channels 102 as described in more detail below.

Figure 4A:
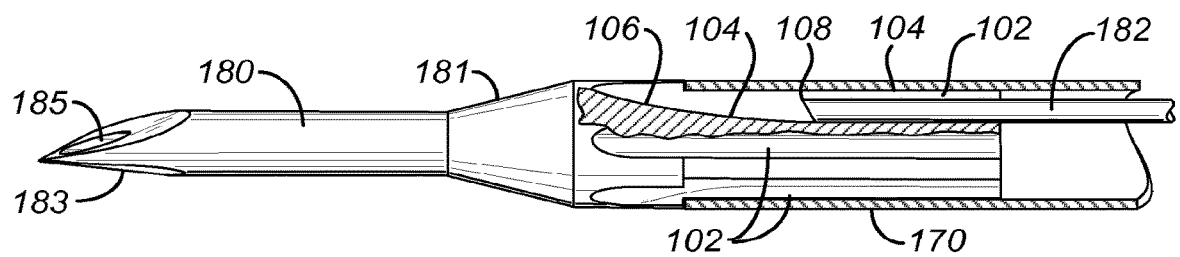
FIGS. 4A-4C illustrate advancement of a single needle electrode through a single deployment channel in the needle electrode deployment shaft of FIG. 1.
Figure 4B:
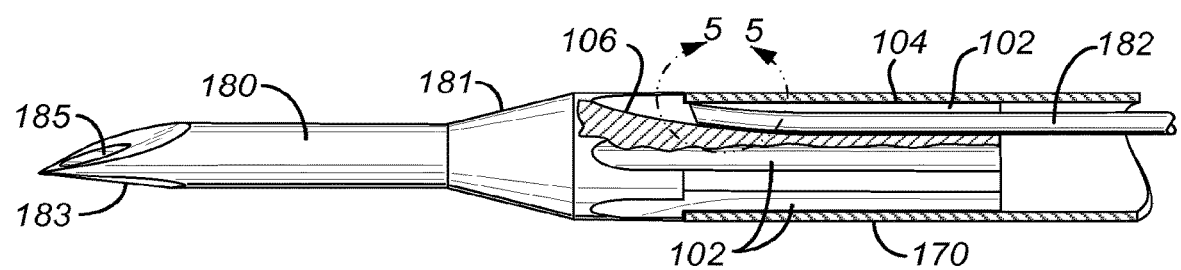
Figure 4C:
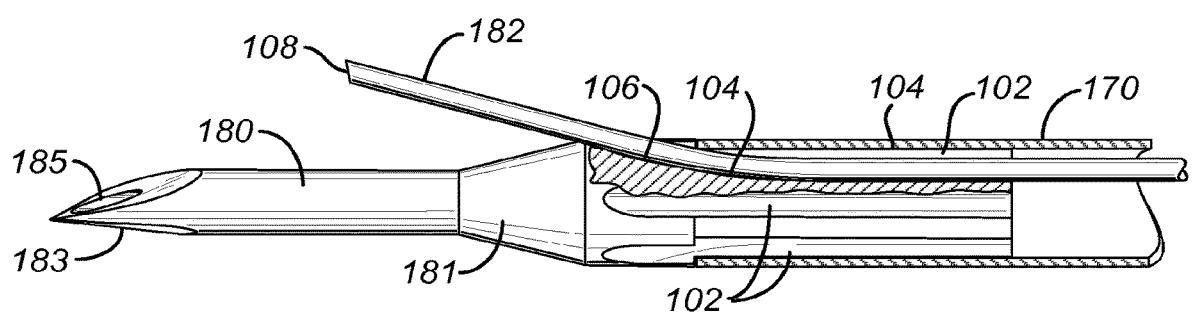
Figure 5:
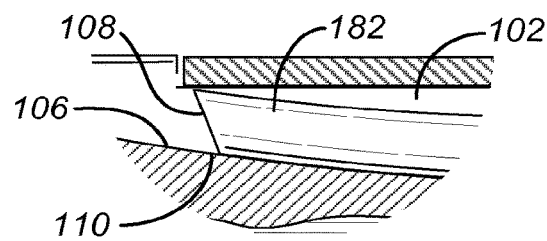
FIG. 5 is a detailed view taken along line 5-5 of FIG. 4B illustrating a chamfered end of the needle electrode passing over the deployment ramp.

The needle advancement channels 102 may be formed in either of two basic configurations. The first of these configurations is illustrated in FIGS. 4A-4C and 5, where the needle advancement channels 102 are aligned axially over the large-diameter portion of the central member 170. The advancement channels 102 comprise a proximal portion 104 and a ramp portion 106 where the proximal portion is disposed in a direction parallel to the axis of the central member 170 while the ramp portion is curved so that it forms a radially outwardly directed surface which deflects the distal tip 108 of the needle electrodes 182 outwardly as shown in the sequence of FIGS. 4A-4C. In particular, as shown in FIG. 5, the distal end 108 is chamfered so that its lower contact point 110 will slide against the surface of ramp 106 without significant seizing or impediment.

Figure 6A:
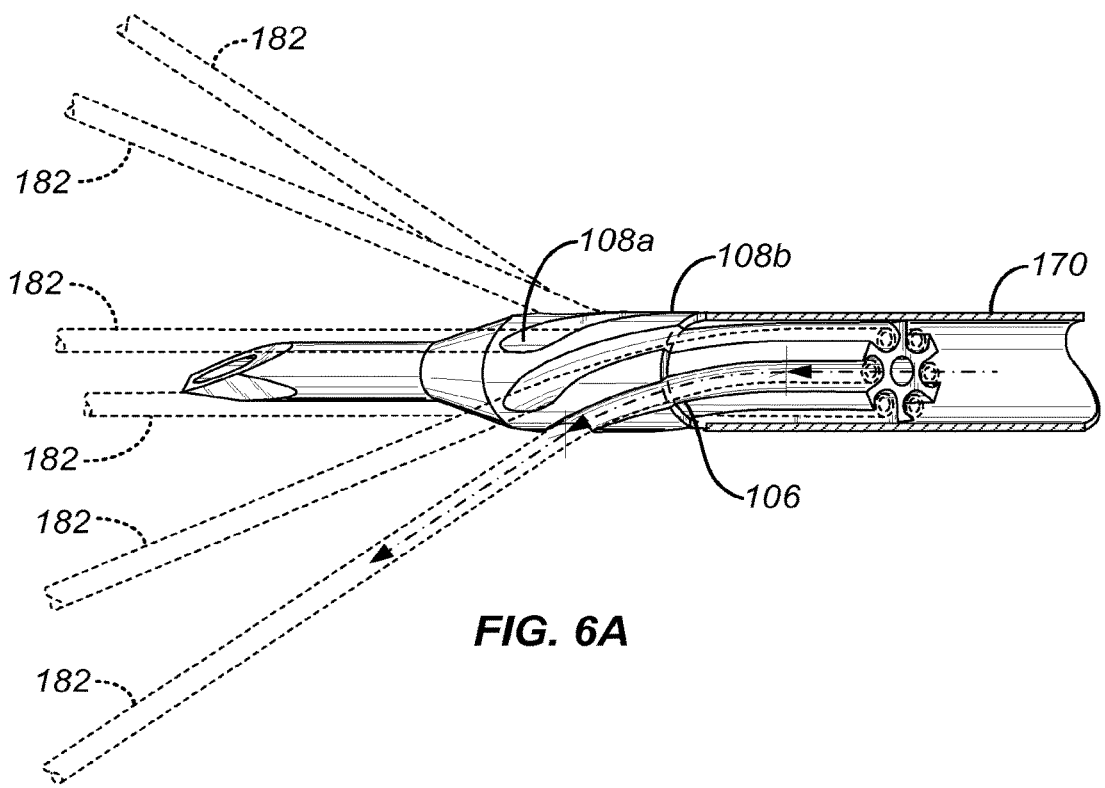
FIGS. 6A-6C illustrate angularly offset needle deployment ramps which are optionally used in the needle electrode deployment shafts of the present invention.
Figure 6B:
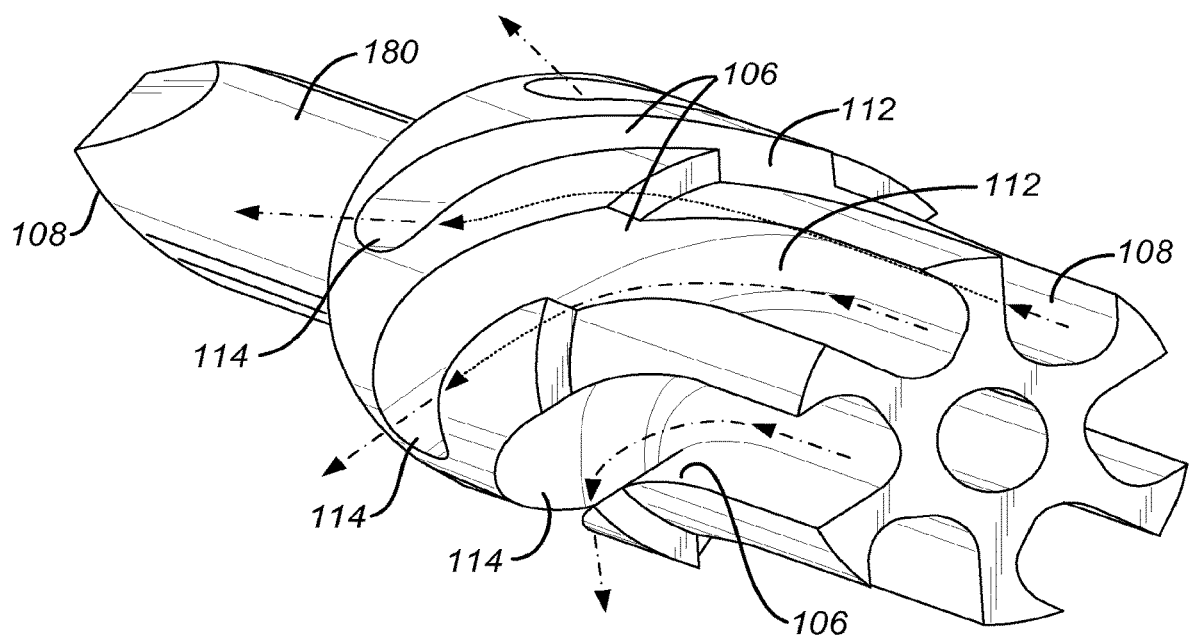

While suitable for many particular applications, the use of axially aligned needle electrode advancement channels 102 is disadvantageous since it has a limited change in radial depth through which the needle can be bent. By employing arcuate or spiral needle paths, as shown in FIGS. 6A-6C, the "radial" distance through which the needle electrodes 182 can be curved radially outwardly within a fixed tip length is increased. As shown in FIGS. 6A and 6B, the needle ramps 106 will have a ramp entrance 112 located at a first angular orientation relative to the longitudinal axis of the central member and a ramp exit 114 located at a second angular orientation relative to the longitudinal axis. By increasing the offset angle .theta. (FIG. 6C) between the entrance 112 and exit 114, the total radial length of the ramp is increased. Thus, the spiral or arcuate ramp geometries allow the needles to be bent through a larger angle (relative to the longitudinal axis of the central member).

Figure 6D:
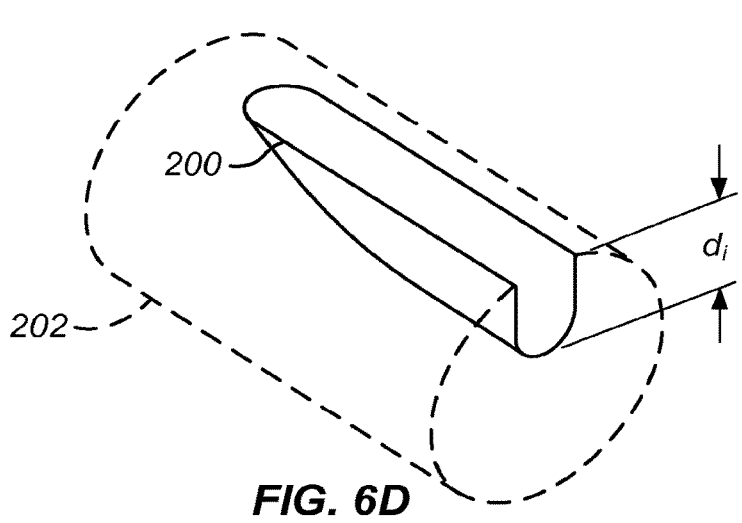
FIGS. 6D-6F illustrate a straight needle deployment ramp and two alternative constructions of the angularly offset needle deployment ramps which may be used in the deployment shafts of the present invention.
Figure 6C:
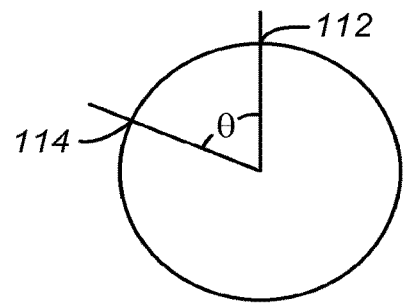
Figure 6E:
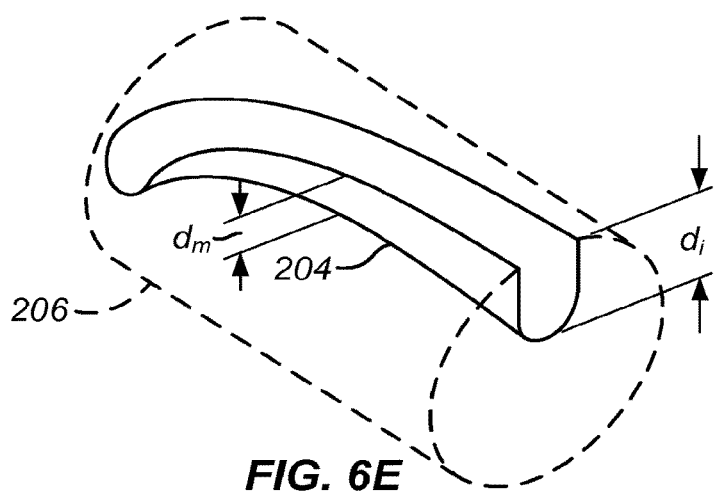
Figure 6F:
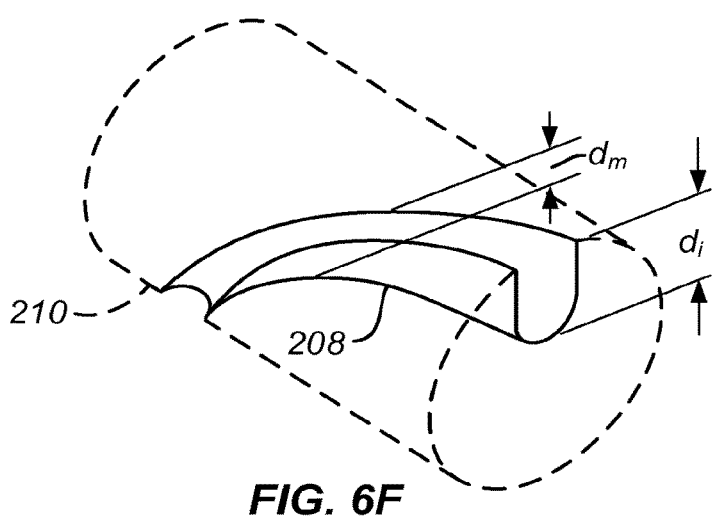

The differences between the straight, simple curved or arcuate, and spiral needle paths are illustrated in FIGS. 6D-6F. In FIG. 6D, a straight needle path 200 is formed in a solid cylindrical body 202 (broken line). It has an initial depth $d_i$ where the depth relative to the outer surface of the cylinder decreases in the distal direction. While a single channel 200 is illustrated, it will be appreciated that multiple channels, typically six, will be formed in the actual device. The channel 200 is formed along an axial path which is parallel to the axis of the cylinder.

A needle ramp 204 having a simple curved or arcuate shape in a cylindrical shaft 206 is illustrated. The initial depth $d_i$ of the ramp 204 may be the same as that in the straight or axial channel 200, and the final depth will be zero in both cases. Thus, while the change in depth will be the same, by curving the needle path or channel 204, the total length of travel of the needle through which it is bent outwardly (away from the central axis of the central member) is increased, thus increasing the needle exit angle for a given needle strain.

The radial component of the needle path or channel, and thus the needle angle, can be increased still further by forming a spiral path 208, as illustrated in FIG. 6F. While an arcuate needle path 204, as illustrated in FIG. 6E, is confined within a plane that intersects the central member, a spiraled needle path spirals around the longitudinal axis of the central member, creating a needle path within this curved surface, the radial component of the needle path (the radial distance between the channel entrance and exit) can be increased versus a needle path confined within a plane.

The needle electrode deployment structures as just described may be employed in a variety of delivery systems for positioning the central shaft in a body and advancing the individual needle electrodes into tissue. Most simply, the central member or main needle shaft can be fixedly attached to a handle with a trigger or lever mechanism coupled to the needle electrodes to selectively advance and retract them within the needle advancement channels 102. In a particular use, the needle electrode deployment structures 100 may be combined in an ablation device having an on-board imaging transducer as described in application No. 61/091,708, the full disclosure of which has previously been incorporated herein by reference. The details of such structures are provided below.

Figure 7:
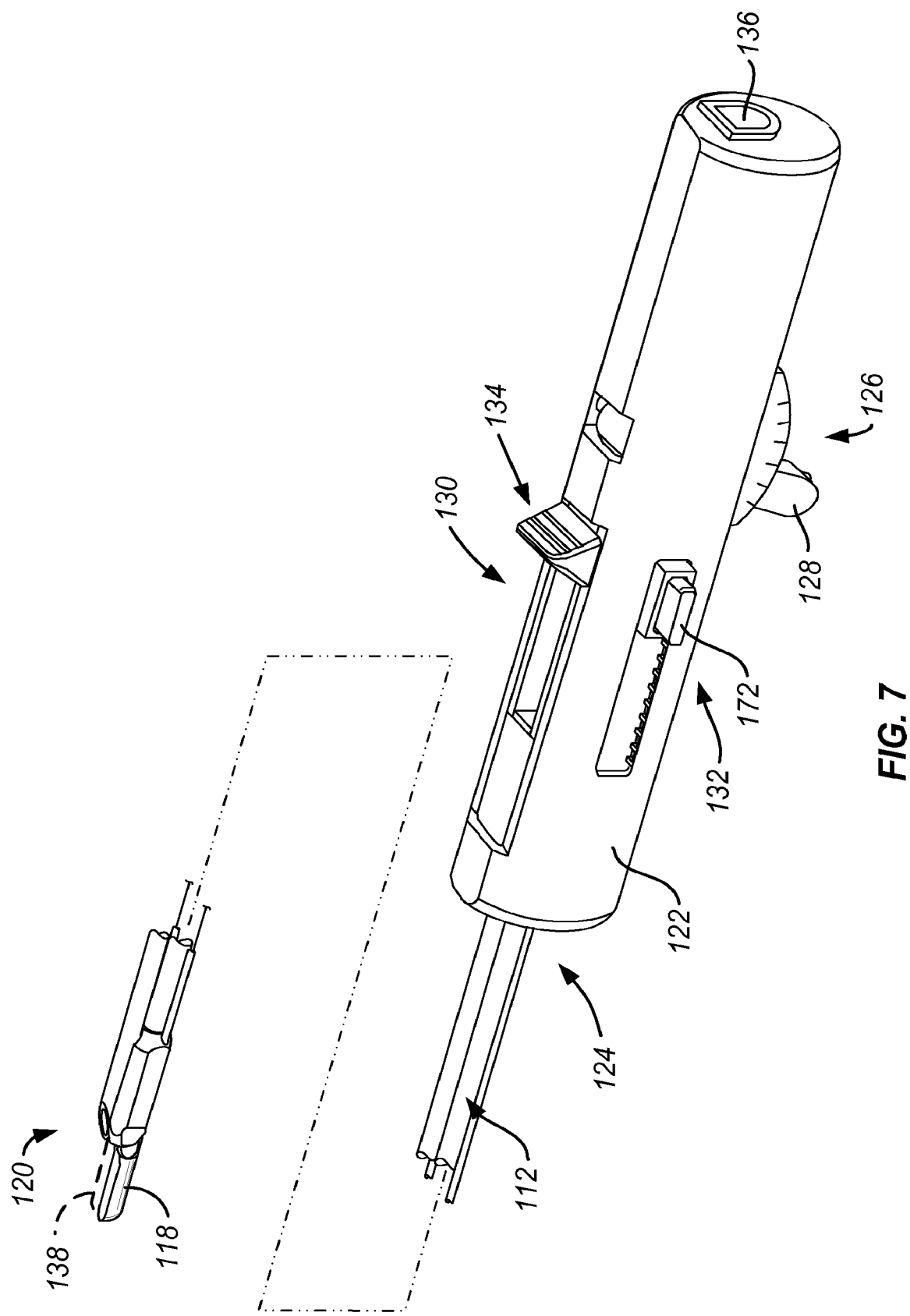
FIG. 7 illustrates a probe having an ultrasonic imaging array which may be used for introducing and deploying needle electrodes from a needle electrode deployment shaft in accordance with the principles of the present invention.
Figure 8:
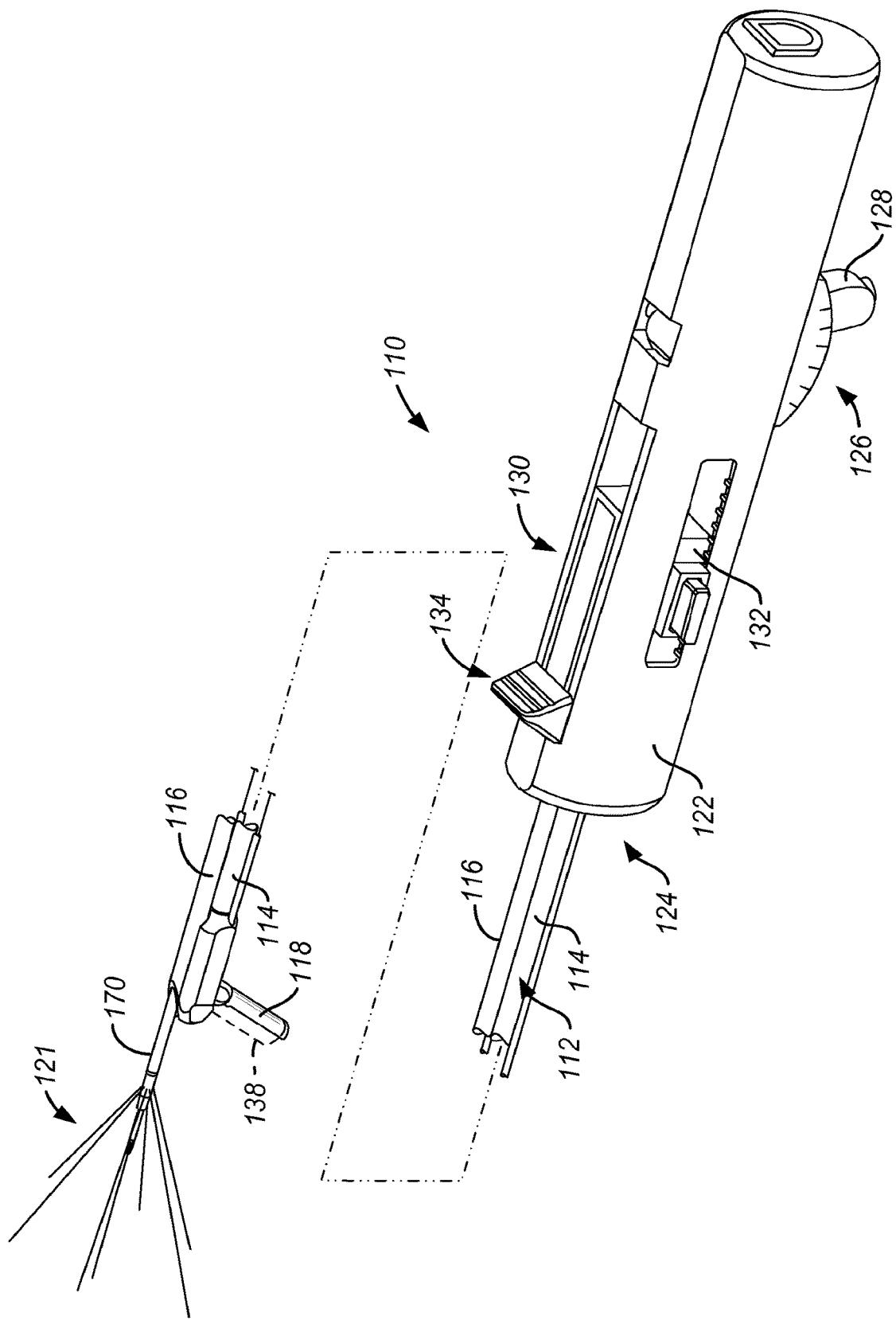
FIG. 8 illustrates the probe of FIG. 7 with the individual needle electrodes being deployed.

Referring to FIGS. 7 and 8, an imaging and therapeutic delivery system 110 constructed in accordance with the principles of the present invention comprises a straight shaft assembly 112 including a hollow tube 114 and a needle tube 116. A tip 118 which is adapted to receive an ultrasonic imaging array (shown in broken line at 138) is pivotally attached to a distal end 120 of the hollow tube 114 of the straight shaft assembly 112. The needle electrode array 121 is deployed through a lumen or central passage in the needle tube 116 at the distal end 120 of the shaft assembly 112. A handle assembly 122 is attached to a proximal end 124 of the straight shaft assembly 112 and includes a pivoting mechanism 126, typically found on its lower surface as illustrated, for selectively pivoting the imaging array tip 118 between a low profile configuration where the tip 118 is axially aligned with the axis of the shaft assembly 112, as illustrated in FIG. 7, and a deflected configuration where the tip 118 is oriented at an acute or right angle relative to the axis of the shaft, as illustrated in FIG. 8. The tip 118 may be placed in its axially aligned, low profile configuration for introduction to the body cavity, for example through the cervix into the uterus, and may be shifted to its deflected configuration in order to image tissue and/or to track deployment of the needle electrode array 121. As described in more detail below, the pivoting mechanism 126 includes a lever 128 which may be manually retracted from the distally advanced configuration shown in FIG. 7 to the proximally retracted configuration shown in FIG. 8 in order to pivot the tip 118.

The handle 122 will also include a delivery needle electrode deployment mechanism 130 which includes a first slide subassembly 132 and a second slide subassembly 134. The handle will usually further include a port 136 at its proximal end. Port 136 allows introduction of an ultrasonic or other imaging core, where the imaging core has an imaging array 138, typically an ultrasonic imaging array as described in detail in copending application Ser. Nos. 11/620,594; 11/620,569; and 11/564,164, the full disclosures of which are incorporated herein by reference. The proximal end of the handle will also allow electrical connections to be made to the needle electrode array. Additionally, the distal end of the handle will usually provide a standard luer connection for the infusion of non-conductive coupling fluids.

Referring now to FIGS. 9-14, operation of the first slide subassembly 132 and the second slide subassembly 134 will be described. For clarity, portions of the pivot mechanism 126 have been removed from these views. Prior to deployment, as shown in FIGS. 9 and 10, the needle electrode array 121 is fully drawn into the central passage of needle tube 116. Needle tube 116 has an open distal tip 164 through which the delivery shaft and needle electrodes will emerge when advanced using the slide subassemblies 132 and 134.

Figure 11:
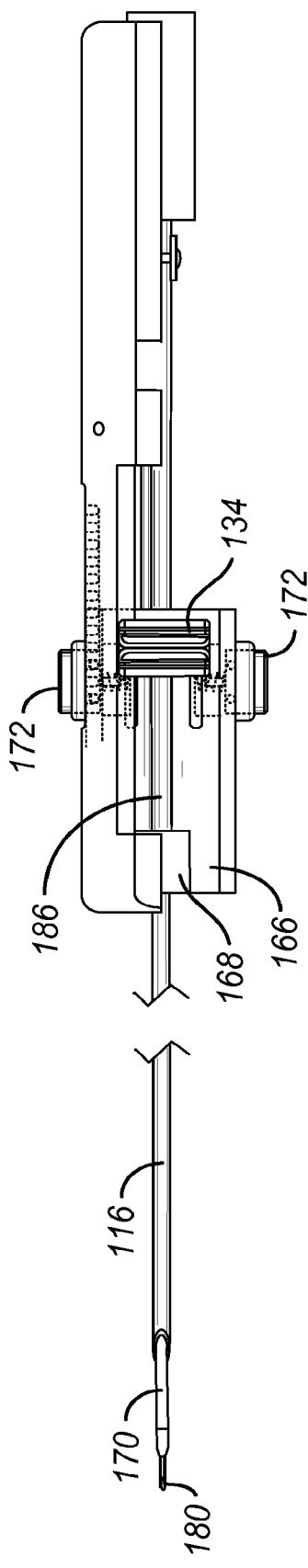
Figure 12:
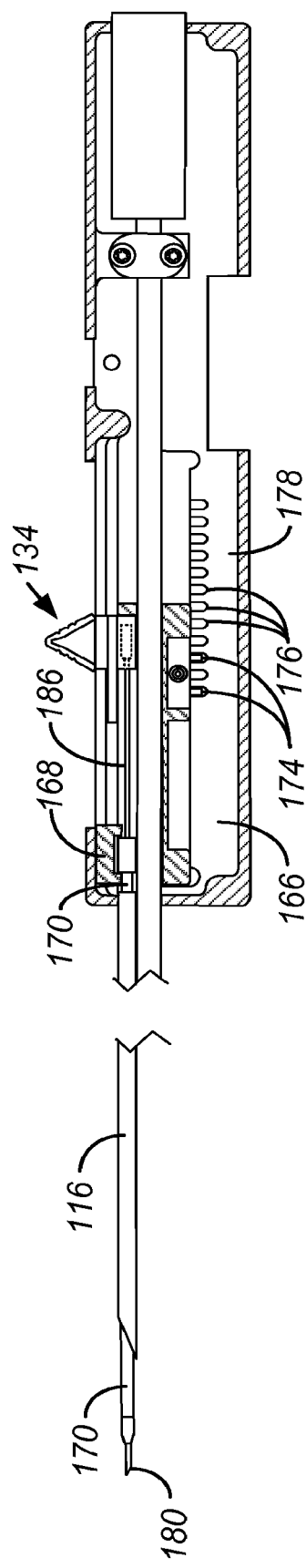

The first slide subassembly 132 comprises a reciprocating carriage 166 having a coupling 168 attached to a proximal end of the needle 170. The carriage 166 may be axially advanced and retracted by manually pressing buttons 172 to disengage pins 174 (FIG. 9) from pockets 176 in a straight locking strip 178. Once the pins 174 are disengaged, the carriage 166 may be distally advanced, as shown in FIGS. 11 and 12, to advance tip 180 of needle 170 from the distal end of the needle tube 116. The buttons 172 may then be released to allow pins 174 to reenter the adjacent pockets 176 in the locking strip 178, thus locking the needle 170 in place.

Referring now in particular to FIGS. 13 and 14, a plurality of radially diverging needle electrodes 182 may be deployed from the distal end of needle 170 using the second slide subassembly 134 which includes a thumb slide 184. The thumb slide 184 is reciprocatably carried in the carriage 166 so that the thumb slide will advance the needle electrodes relative to the needle. The thumb slide is connected to a tube 186 which enters a hollow central passage or lumen of the needle 170 and is coupled to the plurality of needle electrodes 182 so that advancement of the thumb slide 184 from the retracted position shown in FIGS. 11 and 12 to the distally advanced position shown in FIGS. 13 and 14 causes the needle electrodes 182 to emerge from the distal end of the needle 170. The needle electrodes 182 are preferably formed from a straight, resilient metal, such as stainless steel, nickel titanium, or the like, and are deflected outwardly by ramps (FIGS. 4A-4C and 6A-6E) in the distal end of the needle.

Figure 15:
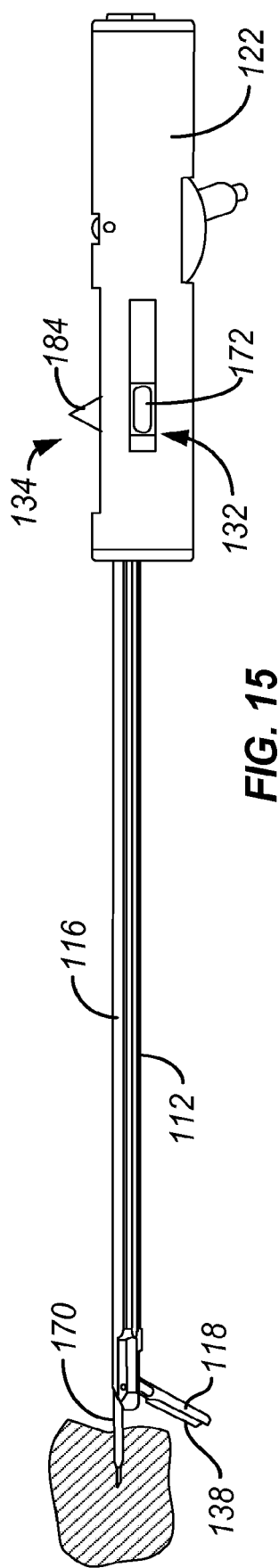
FIGS. 15 and 16 illustrate use of the probe apparatus for introducing needle electrodes into a tissue mass while viewing with the ultrasonic viewing component.
Figure 16:
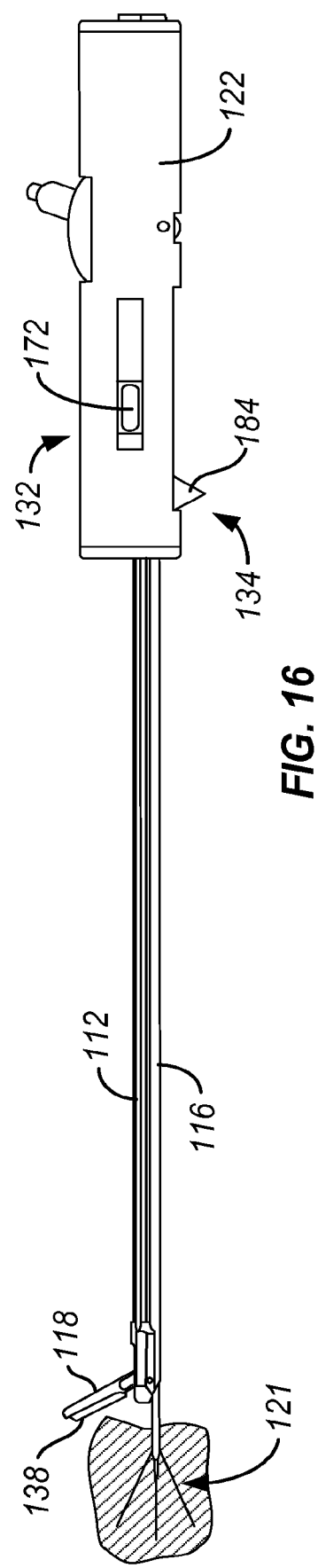

The use of the imaging and therapeutic delivery system 110 of the present invention is illustrated in FIGS. 15 and 16. After imaging using the imaging array 138 carried on or in tip 118, the needle 170 is advanced into target tissue identified by the imaging using the first slide subassembly 132, as shown in FIG. 15. Usually, the position of the tip 118 will be adjusted to assure that travel of the needle 170 into the tissue may be observed. After the location of the needle tip 180 has been confirmed, the thumb slide 184 of the second slide subassembly 134 may then be advanced, as shown in FIG. 16, to extend the needle electrodes 182 into the tissue. In the preferred embodiments of the present invention, the needle 170 and needle electrodes 182 will be rotatably connected to the remainder of the device to allow the handle to be rotated, thus rotating the imaging array 138, to facilitate imaging even after the needle and needle electrodes have been deployed. A significant advantage of such rotatability is that the array can be rotated relative to the shaft to image all of the deployed needle electrodes 182 prior to energizing. The physician can make sure that the electrodes remain safely spaced from the serosa and other sensitive tissue structures prior to energizing.

Figure 17:
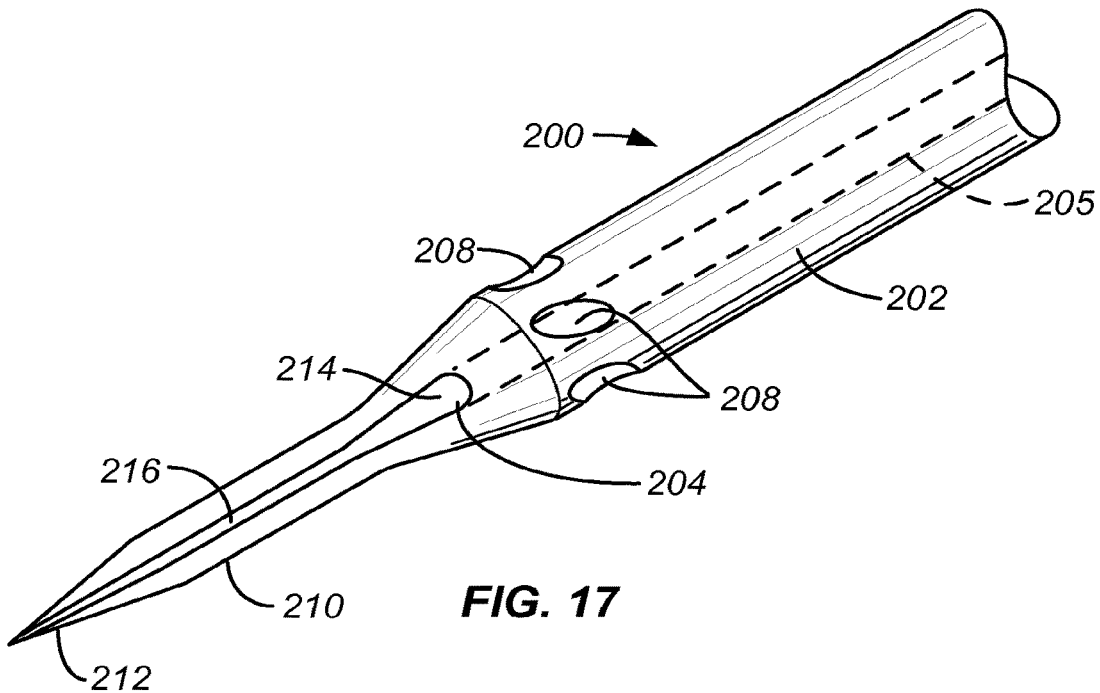
FIG. 17 is perspective view of a needle electrode deployment device having a radially offset spike constructed in accordance with the principles of the present invention.
Figure 18:
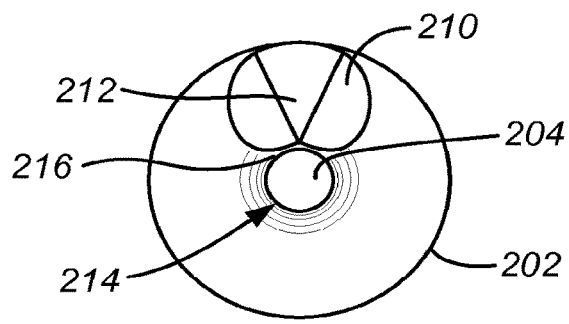
FIG. 18 is an end view of the needle electrode deployment device of FIG. 17.
Figure 19:
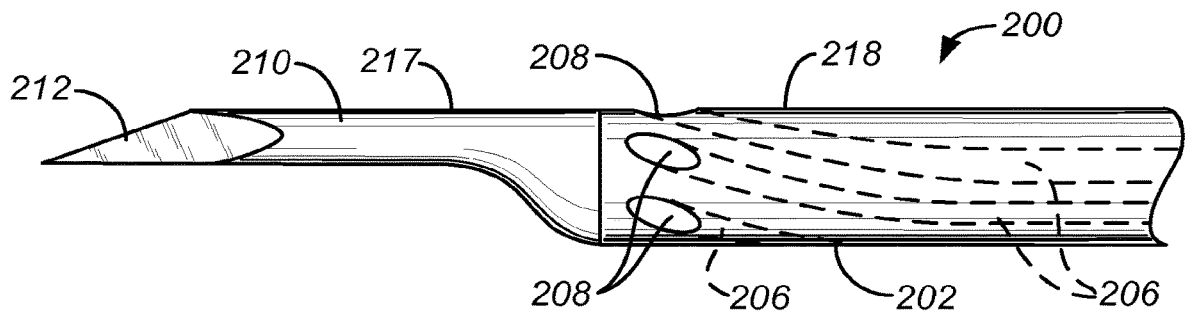
FIG. 19 is a side view of the needle electrode deployment device of FIGS. 17 and 18.

Referring now to FIGS. 17-19, a needle electrode deployment device 200 comprises a central member 202 having a distal end 204 and a proximal end (not shown). The needle electrode deployment device 200 will function similarly to the needle electrode deployment structure 100 described previously and will include an axially aligned electrode advancement passage 205 along its central axis. Usually, the needle electrode deployment device 200 will further include a plurality of outer or peripheral needle electrode advancement channels 206 terminating in peripheral electrode deployment ports 208, again in a manner similar to those described previously with respect to deployment device 100.

In contrast to the previous embodiments, the needle electrode deployment device 200 includes an introducer tip or spike 210 terminating with a faceted cutting tip 212, similar to a trocar cutting tip, to facilitate introduction into tissue as the central member is manually or otherwise advanced in a distal direction through uterine or other solid tissue. The axially aligned electrode advancement passage 205 terminates in a central electrode deployment port 214 which is proximally retracted from the faceted cutting tip 212 of the spike 210, typically by a distance in the range from 1 mm to 10 mm. Preferably, an axial channel or groove 216 is formed along an inner surface of the spike 210, which channel or groove will act as a guide as a central electrode 230 (FIGS. 20A-20C) is advanced from the port 214 of the passage 205 of the central member 202. An outer surface or edge 217 of the introducer tip will typically be straight and aligned with an outer surface 218 of the central member, as best seen in FIG. 19.

The spike 210 has a cross-sectional area which is significantly less than the cross-sectional area of the central member 202. In the illustrated embodiment, the cross-sectional area of the introducer tip 210 is about 25% of the cross-sectional area of the central member 202, but the percentage of decrease can vary within the ranges set forth above in the Summary of the Invention. Usually, the diameter of the central member will be in the range from 0.75 mm to 3 mm, e.g. having a circular cross-section. The cross-sectional area of the introducer tip will usually be in the range from 0.25 mm$^2$ to 5 mm$^2$.

By proximally retracting and radially offsetting the axis of the spike 210 relative to the central electrode port 214 and the central axis of the central member 202, an improved and stabilized geometry is provided for deploying central electrode 230, as illustrated in FIGS. 20A-20C. Initially, as shown in FIG. 20A, the central electrode 230 is retracted within the axially aligned electrode advancement passage 205 with a distal, tissue-penetrating tip 232 of the electrode positioned proximally of the central electrode deployment port 214. By advancing the central electrode 230, using the mechanisms described with previous embodiments, distal tip 232 will be distally advanced into tissue along a generally linear path, as shown in FIG. 20B. The stability and alignment of the needle electrode 230 is partially maintained by traveling through the channel or groove 216 on the inner surface of the introducer tip 210.

After the device 200 has been introduced into tissue and the central electrode 230 and optionally peripheral electrodes (not shown) are advanced into the tissue, the central member 202 can sometimes become misaligned so that the electrode 230 is stressed and bent at the region where it exits from the axially aligned electrode advancement passage 205, as shown in FIG. 20C. By having a rounded peripheral edge 218 surrounding the central electrode port 214, the stress on the needle can be relieved by allowing a more gradual bending radius. Moreover, the rounded peripheral edge also facilitates retracting the electrode 230 as binding and friction are reduced.

Figure 21A:
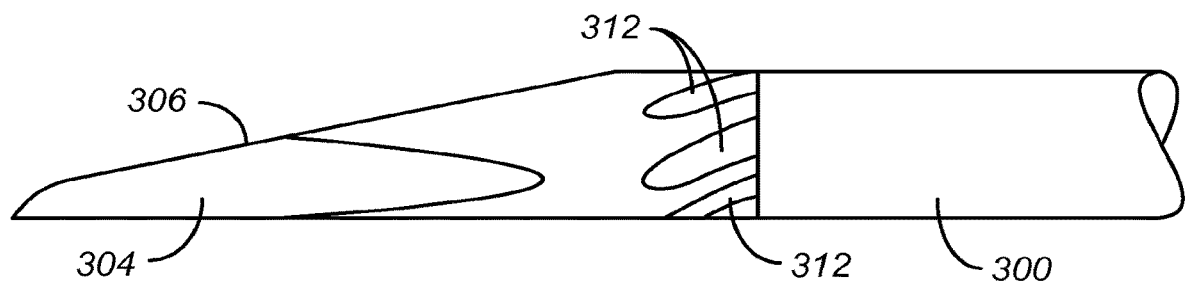
FIGS. 21A-21C illustrate further embodiments of the distal end of the center member of the present invention each of which have a tapered surface with an enlarged needle deployment cavity.
Figure 21B:
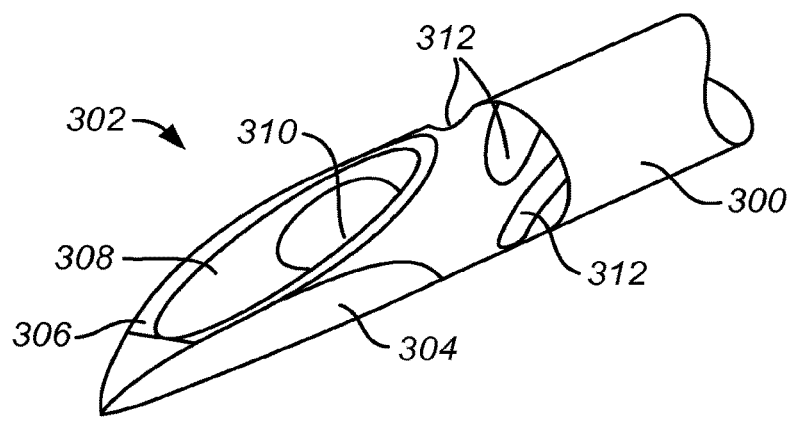
Figure 21C:
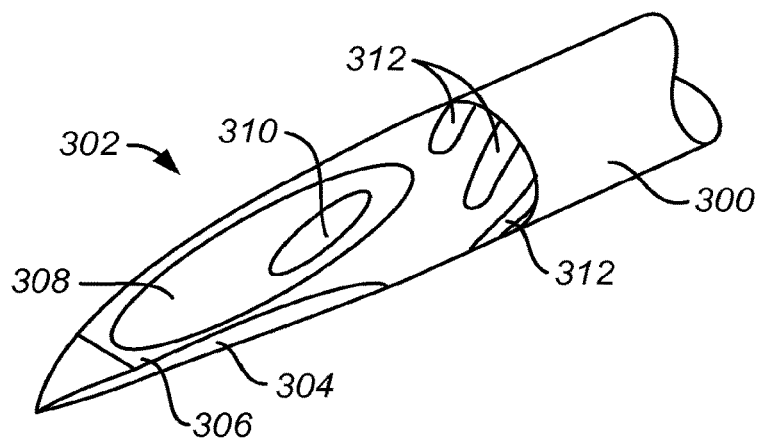

Referring now to FIGS. 21A-21C, a further embodiment of the central member 300 terminates in a spike 302 having a trocar cutting surface 304 and an opposed chamfered surface 306. An electrode transition cavity 308 is formed in the chamfered surface 306 and extends distally from a central electrode port 310, as best seen in FIGS. 21B and 21C. As illustrated, the cavity 308 has a generally ovoid shape, but it could also be spherical, conical, or have some other concave geometry. The exit port 310 may have a tapered geometry, as shown in FIG. 21B, or a more slotted geometry, as shown in FIG. 21C. In both cases, the transition of the central electrode from the central electrode passage through the electrode port 310 into the cavity 308 provides stress relief both as the electrode is advanced and as the central member 300 is manipulated during use. Preferably, the deployment device of FIGS. 21A-21C will include the peripheral electrode channels 312 similar to those described in previous embodiments.

Figure 22A:
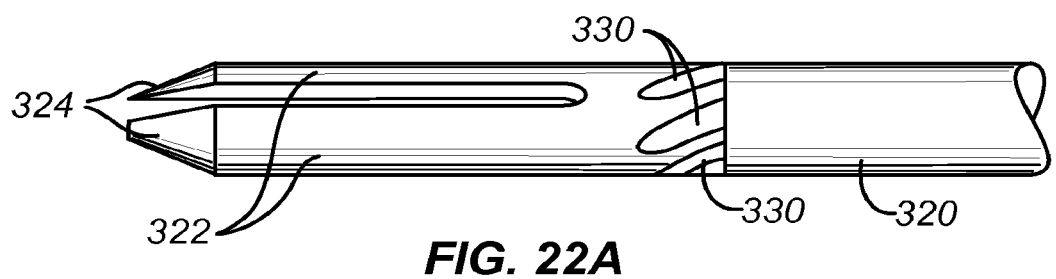
FIGS. 22A-22B illustrate yet another embodiment of the distal end of the center member of the present invention, where the distal end of the center member terminates in a plurality of peripheral spikes.
Figure 22B:
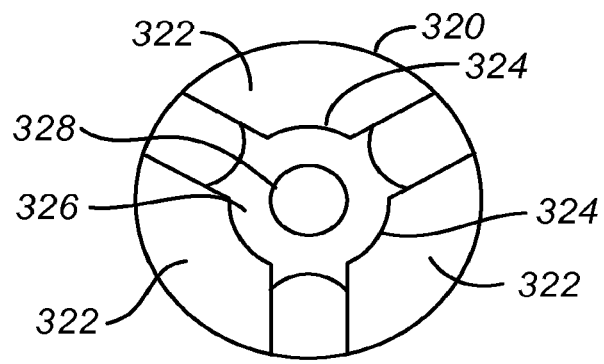
Figure 23A:
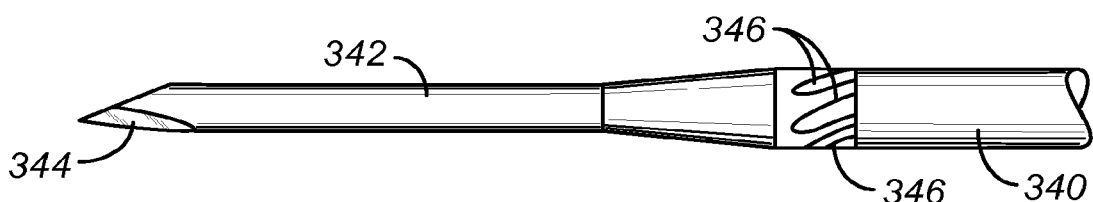
FIGS. 23A-23B illustrate a still further embodiment of the center member of the present invention having a fixed spike at the distal end.
Figure 23B:
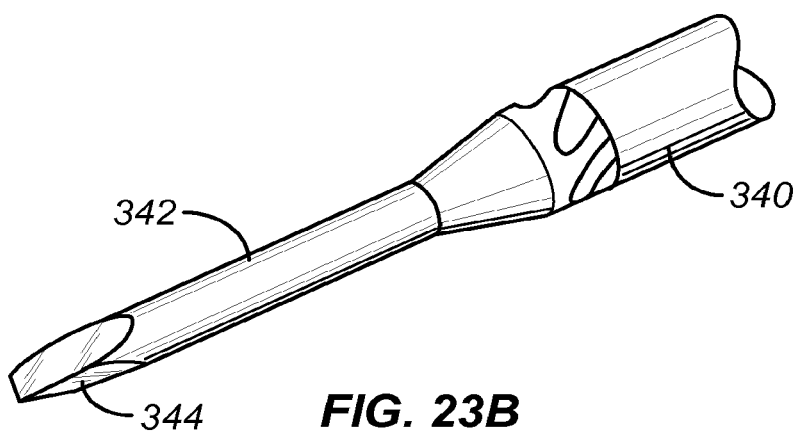

Referring now to FIGS. 22A and 22B, a further embodiment of the distal end of a central member 320 terminates in a plurality of peripherally located axially extending spikes 322. Each of the spikes 322 has a sharpened distal tip 324, and together the spikes 322 define a protected region 326 (FIG. 22B) which extends axially from a central electrode deployment port 328. As with certain of the previous embodiments, the protected region 326 provides for stress relief of the center electrode (not shown) when it is deployed through the electrode deployment port 328.

The embodiment of FIGS. 22A and 22B will also preferably include a plurality of peripheral electrode deployment channels 330 which are similar to those described for previous embodiments.

Another embodiment of a central member 340 comprises a single spike 342 attached to the distal end of the center member. The single spike 342 will preferably be electrically isolated so that it can be connected to a wire to provide RF or other current for treatment. The single spike 342 will preferably terminate in a sharpened tip, such as trocar tip 344 to permit self introduction of the central member 340 through tissue. The central member 340 will preferably include a plurality of peripheral electrode deployment channels 346, which channels are formed generally as described for previous embodiments.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating uterine fibroids, said method comprising:
introducing a probe through a cervix into a uterus;
locating a uterine fibroid using an ultrasonic transducer carried by the probe;
advancing a shaft member from the probe into uterine tissue proximate the uterine fibroid; and
advancing a plurality of needle electrodes in a distal direction from the shaft member through a channel array comprising a plurality of ramps into the uterine fibroid and/or tissue surrounding the uterine fibroid, wherein the ramps are each arcuate and curved about a longitudinal axis of the shaft member; and
delivering energy from the needle electrodes to necrose the fibroid.

2. A method as in claim 1, wherein the energy is radiofrequency energy.

3. A method as in claim 2, wherein the radiofrequency energy is monopolar.

4. A method as in claim 2, wherein the radiofrequency energy is bipolar.

5. A method as in claim 1, further comprising rotating an imaging array about the probe to observe the positions of said plurality of needles prior to delivering energy.

6. A method as in claim 1, wherein the ramps each follow a spiral path.

7. A method as in claim 1, wherein the ramps are each arcuate and confined within a plane that intersects the shaft member.

8. A method as in claim 1, wherein the channel array comprises a plurality of channels and each channel comprises an axially aligned proximal portion and an outwardly directed distal ramp portion such that as the needle electrodes are advanced through the channel, the needle electrodes are deflected radially outwardly as they pass over the distal ramp portion.

9. A method as in claim 1, wherein each ramp has a ramp entrance angularly offset from a ramp exit in a transverse plane.

10. A method as in claim 9, wherein each ramp entrance is located at a preselected radial depth beneath an outer surface of the shaft member and each ramp exit is at the surface.

11. A method as in claim 1, further comprising imaging one or more of the uterine fibroid or needle electrodes using an imaging array.

12. A method as in claim 11, wherein the imaging array is coupled to a distal end of the probe.

13. A method as in claim 11, wherein imaging the one or more of the uterine fibroid or needle electrodes comprises one or more of pivoting or rotating the imaging array about the shaft member of the probe.

14. A method as in claim 11, further comprising pivoting the imaging array between a low profile configuration and a deflected configuration.

15. A method as in claim 14, wherein introducing the probe through the cervix comprises introducing the probe through the cervix while the imaging array is in the low profile configuration.

16. A method as in claim 1, wherein advancing the plurality of needle electrodes in the distal direction from the shaft member through the channel array comprises advancing the plurality of needle electrodes from the shaft member through a lateral side of the shaft member.

17. A method as in claim 1, wherein advancing the plurality of needle electrodes in the distal direction from the shaft member through the channel array comprises advancing the plurality of needle electrodes from the shaft member through a location of the shaft member proximal of a distal end of the shaft member.

18. A method as in claim 1, wherein advancing the plurality of needle electrodes in the distal direction from the shaft member through the channel array comprises advancing the plurality of needle electrodes from the shaft member through a plurality of deployment ports.

19. A method as in claim 18, wherein the ports of the plurality of deployment ports are in the form of a slot, circle, or oval at an angle to a longitudinal axis of the shaft member.

\* \* \* \* \*

UNITED STATES PATENT AND TRADEMARK OFFICE
CERTIFICATE OF CORRECTION

| | |
|---|---|
| PATENT NO. | : 11,564,735 B2 |
| APPLICATION NO. | : 16/417193 |
| DATED | : January 31, 2023 |
| INVENTOR(S) | : Brian Placek |

It is certified that error appears in the above-identified patent and that said Letters Patent is hereby corrected as shown below:

On the Title Page

Column 1, Line 1 (Approx.), under Item (54) Title, delete "FINE" and insert --TINE--.

On Page 4, Column 1, Line 15, under Item (56) Other Publications, delete ""Intrauerine" and insert --"Intrauterine--.

In the Specification

In Column 1, Line 1, delete "FINE" and insert --TINE--.

In Column 1, Line 12, delete "2009" and insert --2009;--.

In Column 1, Line 28, delete "mennorhagia" and insert --menorrhagia--.

In Column 3, Line 6, delete "eligiloy," and insert --elgiloy,--.

In Column 8, Line 38, delete "eligiloy," and insert --elgiloy,--.

Signed and Sealed this
Fifteenth Day of October, 2024

Katherine Kelly Vidal
*Director of the United States Patent and Trademark Office*